United States Patent
Takeyama

(10) Patent No.: US 7,560,097 B2
(45) Date of Patent: Jul. 14, 2009

(54) PHARMACEUTICAL PREPARATION CONTAINING MAGNETIC VESICULAR PARTICLES, MANUFACTURING METHOD THEREOF AND DIAGNOSTIC THERAPEUTIC SYSTEM

(75) Inventor: Toshihisa Takeyama, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 73 days.

(21) Appl. No.: 11/924,961

(22) Filed: Oct. 26, 2007

(65) Prior Publication Data

US 2008/0260648 A1 Oct. 23, 2008

Related U.S. Application Data

(62) Division of application No. 11/268,213, filed on Nov. 7, 2005, now Pat. No. 7,427,393.

(30) Foreign Application Priority Data

Nov. 10, 2004 (JP) ............................ 2004-326431

(51) Int. Cl.
*A61K 49/00* (2006.01)
*A61B 5/055* (2006.01)

(52) U.S. Cl. ................................. 424/9.32; 424/9.321

(58) Field of Classification Search ................ 424/1.11, 424/9.1–9.3, 9.32; 514/2, 59, 60
See application file for complete search history.

(56) References Cited

U.S. PATENT DOCUMENTS

| 5,411,730 A | * | 5/1995 | Kirpotin et al. | .......... 424/9.322 |
| 2003/0211045 A1 | * | 11/2003 | Leszcyznska et al. | .... 424/9.321 |

* cited by examiner

*Primary Examiner*—Michael G Hartley
*Assistant Examiner*—Jagadishwar R Samala
(74) *Attorney, Agent, or Firm*—Lucas & Mercanti, LLP

(57) ABSTRACT

A pharmaceutical preparation containing magnetic vesicular particles is disclosed, wherein the magnetic vesicular particles each include magnetic microparticles within a lipid membrane, an organic compound having at least two groups selected from the group consisting of a hydroxyl group, a carboxyl group, a carbamoyl group, an amino group, a mercapto group, a sulfo group, a dithio group, a thiocarboxyl group and a dithiocarboxyl group is bonded to the magnetic microparticle, and the magnetic vesicular particles satisfy the following equation:

$$0.05 \leq R/(r \times 100) \leq 1.5$$

wherein R represents an average grain size of the magnetic vesicular particles and r represents an average particle size of magnetic microparticles included in the magnetic vesicular particles.

8 Claims, 2 Drawing Sheets

PHARMACEUTICAL PREPARATION CONTAINING MAGNETIC VESICULAR PARTICLES, MANUFACTURING METHOD THEREOF AND DIAGNOSTIC THERAPEUTIC SYSTEM

This application is a Divisional of U.S. patent application Ser. No. 11/268,213 filed Nov. 7, 2005, pending, which, in turn, claimed the priority from Japanese Patent Application No. JP2004-326431, filed on Nov. 10, 2004, both of which are incorporated herein by reference.

FIELD OF THE INVENTION

The present invention relates to pharmaceutical preparations containing magnetic vesicular particles in which magnetic microparticles are bonded with an organic compound, and a manufacturing method thereof, and a diagnostic therapeutic system.

BACKGROUND OF THE INVENTION

Development of "magnetic nano-beads" has been promoted as one of promising medical materials for use in next-generation medical techniques. The magnetic nano-beads (hereinafter, also denoted as magnetic microparticles) are nano-level size microparticles of ferrite (solid solution of $Fe_3O_4$ and $\gamma$-$Fe_2O_3$). Recently, there has been developed a technique of synthesizing them under mild conditions of 4 to 25° C. in the range of a neutral pH, as described in JP-A No. 2002-128523 (hereinafter, the term, JP-A refers to Japanese Patent Application Publication). Magnetic nano-beads for medical use have been proposed, in which drugs or physiologically active materials are allowed to be fixed onto (attached to or included in) the magnetic microparticles covered with dextran, lipid, liposome, polymer or the like, as described in JP-A Nos. 2002-128523 and 9-110722. As application of such magnetic microparticles in the medical field are proposed applications to contrast medium material used for MRI diagnosis or a medicine-transporting carrier, and thermotherapy employing heat generation due to hysteresis loss of magnetic microparticles in the high frequency magnetic field; there was further proposed concurrent performance of diagnosis and therapy of cancer by the combination of both of the foregoing, as described in "BIO INDUSTRY" vol. 21, No. 8, page 48-54 (2004).

Thermotherapy for cancer (Hyperthermia) has been proposed for several decades and is one of the cancer therapies studied. The principle of therapy employs a property of cancer cells being weaker to heat than normal cells, thereby giving therapy with artificially maintaining a high temperature environment. Thermotherapy for cancer is a non-invasive treatment as compared to surgical removal operation which is generally conducted for cancer therapy. Comparing to chemotherapy or radiotherapy which often results in adverse effects, it is selective and its adverse effect becomes lower. Thus, it is a treatment which makes preservation of organs feasible and enhances the patient's quality of life. It is therefore a treatment suitable for an early cancer, or aged persons or infants who are intolerable to operative invasion or adverse effects. Conventional thermotherapy has employed techniques such as induction heating or focused ultrasonic heating and a recent alternate magnetic field heating using a ferrite type MRI contrast medium, and each of these therapies has merits and demerits. Accordingly, there is studied the possibility of using the above-described ferrite type particles as a novel heat-generating element in the alternating magnetic field, as described in "BIO INDUSTRY" vol. 21, No. 8, page 48-54 (2004).

Feasibility of putting employment of magnetic microparticles into practice in the medical field relies on capability of maintaining a physiologically active material, a treatment drug or the like within the beads or capability of its selective delivery to an intended site (targeting capability). In this regard, the magnetic vesicular particles which have been proposed so far, still leave room for improvement. In enclosure of magnetic microparticles within liposome vesicles, various problems relating preparation of the liposome, for example, residue of organic solvents and stability of a liposome structure retard its practical use.

SUMMARY OF THE INVENTION

It is an object of the present invention to provide a pharmaceutical preparation containing magnetic vesicular particles which enables selective delivery of agents to a tumor site (targeting capability), is applicable to a contrast medium material or drug transport carrier and is also usable in thermotherapy employing heat-generation, and diagnosis and treatment of cancer by the combination thereof, and a manufacturing method thereof and a diagnostic therapeutic system by use thereof.

One aspect of the invention is directed to a pharmaceutical preparation comprising magnetic vesicular particles, wherein the magnetic vesicular particles each include one or more magnetic microparticles within a lipid membrane, the magnetic microparticles are each bonded to an organic compound having in its molecule at least two bonding groups selected from a hydroxyl group, a carboxyl group, a carbamoyl group, an amino group, a mercapto group, a sulfo group, a dithio group, a thiocarboxyl group and a dithiocarboxyl group, and the magnetic vesicular particles satisfy the following equation:

$$0.05 \leq R/(r \times 100) \leq 1.5$$

wherein R represents an average grain size of the magnetic vesicular particles and r represents an average particle size of the whole magnetic microparticles included in the magnetic vesicular particles.

The magnetic vesicular particles preferably satisfy the following equation:

$$0.05 \leq R/(r \times 100) \leq 1.0$$

It is preferable that the magnetic microparticles are formed at a pH of 7 to 10 and a temperature of 3 to 30° C. in the presence of an organic compound having at least two groups selected from a hydroxyl group, a carboxyl group, a carbamoyl group, an amino group, a mercapto group, a sulfo group, a dithio group, a thiocarboxyl group and a dithiocarboxyl group.

It is preferable that the average particle size (r) of the magnetic microparticles be within the range of 1 nm to 30 nm and the main component of the magnetic microparticles be a ferrite.

It is preferable that the magnetic vesicular particles which include one or more magnetic microparticles within a lipid membrane are liposome particles (or vesicles), and the surface electric charge of the liposome is positive.

The preparation containing cover magnetic grains are used preferably as an imaging agent and/or a therapeutic agent for tumor.

In the preparation containing magnetic vesicular particles, a physiologically active material and/or an antitumor-active material are bonded directly or via a linkage substance to the surface of the lipid membrane. The imaging agent is used preferably as a contrast medium for use in an ultrasonic imaging diagnostics, a nuclear magnetic resonance imaging diagnostics or an X-ray imaging diagnostics.

When the preparation containing magnetic vesicular particles is used as an imaging agent (or a contrast medium) in an ultrasonic imaging diagnosis apparatus, a nuclear magnetic resonance imaging diagnosis apparatus or a radiographic image diagnosis apparatus, performing scans within not less than 1 min. and not more than 48 hr. after the preparation containing magnetic vesicular particles is dosed into the vein of an examinee, can result in enhanced capability to detect tumorous tissue.

On the other hand, when the preparation containing magnetic vesicular particles is injected into the region near tumorous tissue of an examinee, enhanced capability of detecting tumorous tissue can be achieved by performing scan within not less than 0.5 min. and not more than 36 hr. after the start of injection, using an ultrasonic imaging diagnostic apparatus, a nuclear magnetic resonance imaging diagnostic apparatus or a radiographic imaging diagnostic apparatus.

In the preparation containing magnetic vesicular particles, preferably, at least one selected from a physiologically functional material, additively stabilizing material, medicinally active material, medicinally active chelating material, antitumor-active material, immunopotentiating material, cell fusion material, and gene transfer mediating material is bonded directly or via a linking material to the outermost layer of the lipid membrane.

The above-described therapeutic agent is preferably an agent used for thermotherapy and the thermotherapy is performed, while being subjected to exposure to energy. The exposure to energy enables raising the temperature of the tumorous tissue in the close vicinity of the magnetic vesicular particles. The exposure to energy is preferably exposure to an alternating magnetic field or exposure to ultrasonic waves and of these, exposure to an alternating magnetic field at a frequency of 25 to 500 kHz is specifically preferred.

When the preparation containing magnetic vesicular particles is used as a therapeutic agent, exposing an examinee to an alternating magnetic field or ultrasonic waves within not less than 1 min. and not more than 48 hr. after the preparation containing magnetic vesicular particles is dosed into the vein of the examinee, the temperature of a tumorous tissue can be raised in the close vicinity of the magnetic vesicular particles.

On the other hand, when the preparation containing magnetic vesicular particles is injected to the region near a tumorous tissue of an examinee for use as a therapeutic agent, exposure of the examinee to an alternating magnetic field or ultrasonic waves, within not less than 0.5 min. and not more than 36 hr. after the start of injection, can raise the temperature of a tumorous tissue in the close vicinity of the magnetic vesicular particles.

The manufacturing method of the preparation containing magnetic vesicular particles of the invention comprises mixing a lipid membrane constituents and supercritical carbon dioxide and adding a dispersion of magnetic microparticles with an attached organic compound, followed by discharge of carbon dioxide, whereby the magnetic microparticles are covered with a lipid membrane to form magnetic vesicular particle(s).

The magnetic vesicular particles are formed preferably under conditions of a pH of 7 to 10 and a temperature of 3 to 30° C. in the presence of an organic compound having at least two groups selected from a hydroxyl group, carboxyl group, carbamoyl group, amino group, mercapto group, sulfo group, dithio group, thiocarboxy group and dithiocarboxy group.

The diagnostic therapeutic system of this invention is a system for performing diagnosis of a tumor site of an examinee and therapy thereof, using the above-described preparation containing magnetic vesicular particles. The diagnostic therapeutic system comprising:

an automatic injection device to automatically inject the preparation containing magnetic vesicular particles into an examinee, a diagnosis device provided with a first exposure section to subject the preparation-injected examinee to a first exposure to an ultrasonic, an electromagnetic wave or an X-ray, and an imaging section to scan a tumor site in which the magnetic vesicular particles have been accumulated by the first exposure, a therapy device provided with a second exposure section to subject the magnetic vesicular particle-accumulated tumor site to a second exposure to an alternating magnetic field or an ultrasonic, and a temperature measurement section to measure the temperature of the tumor site and that of a normal site near the tumor site during the second exposure to an alternating magnetic field or an ultrasonic, and a control device which is connected to each of the automatic injection device, the diagnosis device and the therapy device through a network, controls the operation of each of these devices and performs control among these devices.

The above-described temperature measuring section preferably conducts temperature measurement which is non-invasive for the examinee and the non-invasive temperature measurement calculates the temperature from a vertical relaxation time by a signal intensity method, a proton chemical shift by a phase method or a diffusion coefficient by a diffusion image method, each of which uses a nuclear magnetic resonance imaging apparatus, or from values obtained in microwave radiometry using plural frequencies.

It is preferred that the temperature measurement section measures the temperature of a tumor site and that of a normal site near the tumor site and successively transmits measurement results to a control device, and when the control device confirms from the received measurement results that the tumor site has risen to a prescribed temperature, the control device transmits an instruction to stop the exposure to the alternating magnetic field or the ultrasonic to the second exposure section, thereby controlling therapy.

It is also preferred that the second is so controlled that the second exposure section exposes the magnetic vesicular particle-accumulated tumor site to an alternating magnetic field or an ultrasonic, while the first exposure section exposes the tumor site to an ultrasonic, an electromagnetic wave or an X-ray and the imaging section scans the magnetic vesicular particle-accumulated tumor site to confirm the location of the tumor site, whereby therapy is performed with confirming the tumor site.

The magnetic vesicular particles contained in the preparation of this invention enables selective delivery to a disease site or a tumor focus (targeting capability). Accordingly, the preparation is not only applicable to a therapeutic agent, a contrast medium and a drug transporting carrier but is also usable in thermotherapy employing heat-generation, and further usable in diagnosis and therapy of cancer by combinations of the foregoing.

According to the manufacturing method of this invention, the preparation containing magnetic vesicular particles can be made without using any organic solvent so that the obtained preparation exhibits high safety to a living body.

In the diagnostic therapeutic system of this invention, examination, diagnosis and therapy of a disease site or a tumor focus can be conducted as a single system. Accordingly, diagnosis and therapy which have conventionally been conducted separately, can be done concurrently or continuously, thereby lessening the burden given to the patient.

PREFERRED EMBODIMENTS OF THE INVENTION

The preparation of this invention contains magnetic vesicular particles and optionally auxiliary agents.

Figure 1:
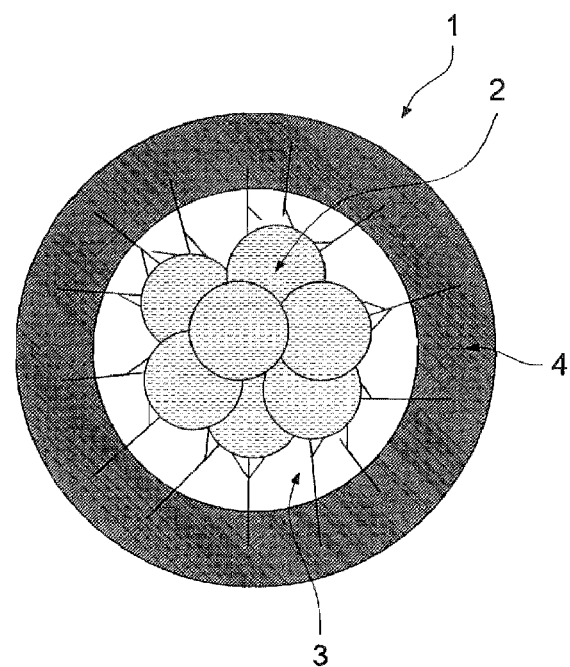
FIG. 1 illustrates a magnetic vesicular particle contained in the preparation of the invention, and plural magnetic microparticles are enclosed within the grain.

As shown in FIG. 1, magnetic vesicular particle 1 is formed by covering magnetic microparticle(s) 2 with lipid membrane 4, i.e., by including the magnetic microparticles within the lipid membrane, in which organic compound 3 having at least two groups selected from a hydroxyl group, a carboxyl group, a carbamoyl group, an amino group, a mercapto group, a sulfo group, a dithio group, a thiocarboxyl group and a dithiocarboxyl group (hereinafter, also denoted simply as organic compound 3) is bonded to the magnetic microparticle(s) 2 though a chemical bond. FIG. 1 shows an embodiment of the magnetic vesicular particle in which plural magnetic microparticles are included within a lipid membrane, but a single magnetic microparticle may be included within a lipid membrane. In one aspect, the magnetic vesicular particles satisfy the following equation:

$$0.05 \leq R/(r \times 100) \leq 1.5$$

wherein R represents an average grain size of the magnetic vesicular particles and r represents an average particle size of the magnetic microparticles.

Figure 2:
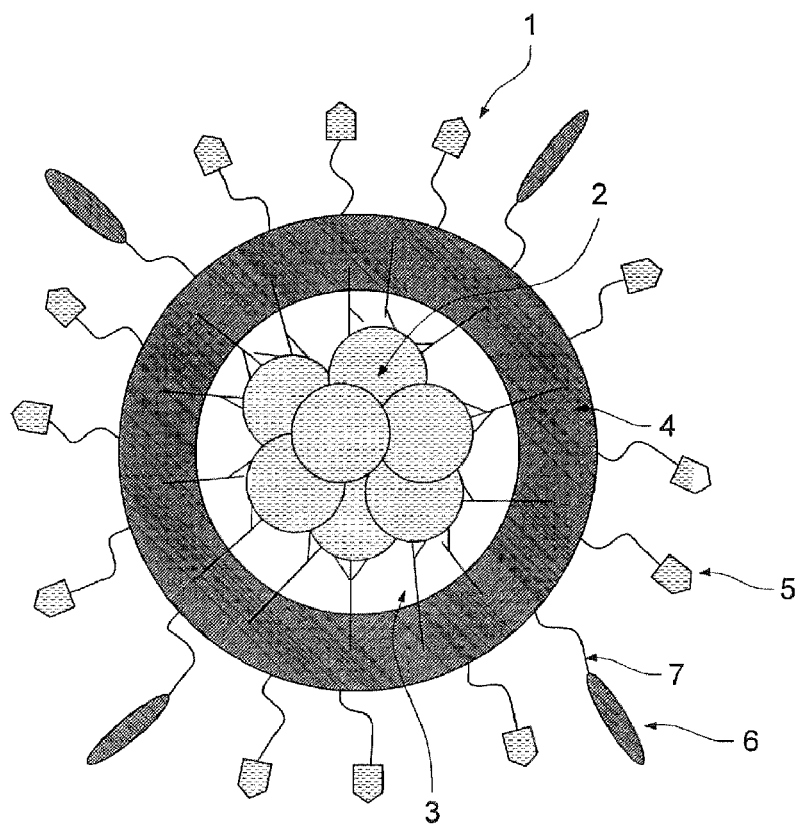
FIG. 2 also illustrates the magnetic vesicular particle.

In the magnetic vesicular particle 1 used in this invention, as shown in FIG. 2, the magnetic microparticle(s) 2, chemically bonded to the organic compound 3, are covered with the lipid membrane 4, the surface of which is preferably bonded via linkage material 7 to physiologically functional material 5 such as an antibody or antitumor-active material 6. Although FIG. 2 shows an embodiment of the magnetic vesicular particle in which plural magnetic microparticles are covered with lipid membrane, a single magnetic microparticle may be covered with lipid membrane. In FIG. 2, a physiologically functional material and an antitumor-active material are bonded but there may also be bonded at least one physiologically active material selected from physiologically functional materials, additionally stabilizing material, medicinally active material, medicinally active chelate material, antitumor-active material, immunopotentiation material, cell fusion material and gene transfer mediator material to be described later. As a result of bonding to physiologically active material, the magnetic vesicular particles are delivered to the tumor site not only for detection but also exerts a specific effect on tumorous tissue. Accordingly, it is usable as a contrast medium exhibiting superior detectability for tumorous tissue and in thermotherapy using energy exposure such as exposure to an alternating magnetic field or exposure to a ultrasonic wave, it raises the temperature of tumorous tissue in the close vicinity of the magnetic vesicular particles and is also usable as a therapeutic agent which is capable of allowing physiologically active material to act onto the tumorous tissue. FIGS. 1 and 2, each illustrates a magnetic vesicular particle contained in the preparation of this invention but specific embodiments are by no means limited to these.

In the specification, "cancer" refers to a malignant tumor and it is also referred to simply as "tumor". The expression, being enclosed within lipid membrane or liposome membrane means being included in the liposome membrane or liposome and associated with the lipid membrane, or existing in a water phase (internal water phase) enclosed in the interior of the lipid membrane.

Magnetic microparticles usable in this invention can use, as a main component, any one of magnetite, $Fe_2O_3$, $Fe_3O_4$, mixed ferrite, and other iron-containing compounds including organic ferromagnetic material. Of these, ferrite, $Fe_3O_4$ exhibiting a maximum force, which is superior in magnetic responsibility, is specifically preferred. There was developed a technique in which nano-sized microparticles of ferrite (solid solution of $Fe_3O_4$ and $\delta$-$Fe_2O_3$) exhibiting superior magnetic characteristics were synthesized by a controlled precipitation method under mild conditions of a temperature of 4 to 25° C. and a neutral pH, as described in JP-A No. 2002-128523. The preparation of this invention employs such mixed ferrite microparticles as suitable magnetic microparticles. Magnetic microparticles having the foregoing ferrite as a core can further contain various metal elements such as Zn, Co and Ni to control magnetic characteristics.

The average particle size of the magnetic microparticles is usually from 1 to 30 nm, preferably from 5 to 25 nm, and more preferably from 5 to 20 nm.

The magnetic vesicular particles, each contains at least one magnetic microparticle as a ferrite core. The number of magnetic microparticles is variable depending on the average size of magnetic microparticles, the average size of magnetic vesicular particles and magnetic characteristics required as the preparation of this invention, therefore, the number of magnetic microparticles is optimally adjusted.

Regarding the average grain size of magnetic vesicular particles having at least one magnetic microparticle, it is necessary to take sizing of the grain size into account to maintain passive targeting capability. Japanese Patent No. 2619037 describes that removal of liposomes of particle sizes of 3000 nm or more can avoid embolization of pulmonary capillaries. However, liposomes of sizes of 150 to 3000 nm are not always antitumorous. It therefore needs to optimally design the particle size according to the objective of the contrast medium. In this invention, the average grain size of magnetic vesicular particles is usually from 50 to 300 nm, preferably from 50 to 200 nm, and from 50 to 150 nm. For example, to achieve selective delivery to the tumor site, the average grain size from 80 to 150 nm is specifically preferred. Making the grain size uniform within 100 to 200 nm (preferably 110 to 130 nm) enables to allow magnetic vesicular particles to be selectively concentrated to cancerous tissue (EPR effect). Pores of neovascular walls existing in solid cancerous tissue are extraordinarily large, as compared to the pore size of capillary wall fenestra of normal tissue, 30 to 80 nm and even molecules having a size of ca. 100 nm to ca. 200 nm leak from the vascular wall. The EPR effect is due to the fact that a neovascular wall existing in cancerous tissue exhibits higher permeability than a microvascular wall, so that blood retention capability have to be enhanced. The magnetic vesicular particles are not so large and are difficult to become a target of capture by a reticulated endothelial cell.

In cases when the preparation of this invention is used as a contrast medium, the average size of magnetic vesicular particles which falls within the foregoing range results in enhanced detection capability of cancerous tissue. On the other hand, in cases when the preparation of this invention is used as a therapeutic agent for use in thermotherapy for tumor and when an average grain size falls within this range, the temperature of tumorous tissue close to the magnetic vesicular particles is limitedly raised upon energy exposure, substantially without affecting normal tissue. When the energy exposure is exposure to an alternating magnetic field, the average size of magnetic microparticles is preferably not less than 10 nm in terms of rotatability of the magnetic microparticles under the alternating magnetic field. An average particle size of less than 10 nm results in poor rotation of the magnetic microparticles, leading to a deteriorated temperature increasing efficiency. Specifically, the average particle size is usually from 10 to 30 nm, preferably from 10 to 25 nm, and more preferably from 10 to 20 nm.

Magnetic microparticles are desirably as large as possible from the viewpoint of contrast performance (specifically, T2 relaxation time) of a contrast medium for use in the nuclear magnetic resonance imaging or simply magnetic resonance imaging (MRI) or from the viewpoint of function as a heat-generating element of thermotherapy, with considering that the particle size and the magnetic moment are dependent on each other, affecting their effects. On the other hand, the grain size of magnetic vesicular particles is limited to be not more than a prescribed size from various biological characteristics, specifically, target directionality. Accordingly, as a preferable range of the average size to find a compromise point between both parameters, the magnetic vesicular particles are required to satisfy the following equation, indicating the relationship between the particle size of magnetic microparticles and the grain size of magnetic vesicular particles:

$$0.05 \leq R/(r \times 100) \leq 1.5,$$

preferably, $0.05 \leq R/(r \times 100) \leq 1.0$, and more preferably, $0.05 \leq R/(r \times 100) \leq 0.8$, wherein R represents the average grain size of magnetic vesicular particles and r represents the average particle size of magnetic microparticles included in the magnetic vesicular particles.

When the magnetic vesicular particles satisfy the foregoing equation, sizes of constituent magnetic microparticles and the size of the whole particles are guaranteed to fall within the suitable range. Thereby, the magnetic vesicular particles can be delivered specifically to the tumor site. As a result, the magnetic vesicular particles are usable as a contrast medium capable of enhancing detection capability or usable as a therapeutic agent capable of limitedly raising the temperature of tumorous tissue in the close vicinity of the magnetic vesicular particles in thermotherapy accompanying with energy exposure such as exposure to an alternating magnetic field or exposure to a ultrasonic wave.

The organic compound chemically bonded to magnetic microparticles is one which has in its molecule at least two binding groups (a) selected from hydroxyl group (—OH), carboxyl group (—COOH), carbamoyl group (—CONH$_2$), amino group (—NH$_2$), mercapto group (—SH), sulfo group (—SO$_3$H), dithio group (—SS—), thiocarboxyl group [—C(S)OH or —C(O)SH] and dithiocarboxyl group (—CSSH). Herein, the expression, chemically bonded means being bonded through chemical bond. In general, the chemical bond is classified to covalent bond, ionic bond, metallic bond and coordinate bond (including chelate bond). The organic compound may be bonded to the magnetic microparticles through any of the foregoing chemical bonds. These groups (a) are each chemically bonded to the magnetic microparticle surface, whereby polyvalent bonding effects of the organic compound are displayed. Thus, the organic compound is bonded to the magnetic microparticles through at least two binding groups, forming strong linkage to the magnetic microparticles. Such a poly-binding organic compound allows plural magnetic microparticles to be connected to each other and is further bound to lipid membrane 4 covering magnetic microparticle(s) 2, playing the role as a connector. As a result, magnetic vesicular particles are entirely structurally stabilized. Magnetic microparticles can stably be enclosed within lipid membrane by the existence of organic compound 3. In one case, the organic compound bonding to the magnetic microparticle may be linked at the other end to physiologically active material or medicinally effective material. Lipophilic physiologically active material or medicinally effective material which is delivered by magnetic vesicular particles as a carrier is expected to preferably interact with lipid membrane 4 covering magnetic microparticle(s) 2.

Such organic compound is not specifically limited if it has at least two binding groups (a). The binding groups (a) may be an identical functional group or may be a combination of different functional groups. Specific examples thereof include an organic compound which contains a hydrogen atom or an organic group (b) at the prescribed carbon position of compound (A) having at least two binding groups (a). A compound which has a branched structure at least one end of the compound skeleton is preferred.

Examples of a compound forming a basic skeleton of the compound (A) include phthalic acid, isophthalic acid, terephthalic acid, succinic acid, glutaric acid, adipic acid, pimelic acid, fumaric acid, maleic acid, 2-mercaptoamine, 6-aminehexanethiol, 2-mercaptopropionic acid, asparagic acid, glutamine, malic acid, oxaloacetic acid, 2-ketoglutaric acid, serine, threonine, cysteine, cysteic acid, cystine, N-acetylcysteine, cysteine ethyl ester, and dithiosraytol. A single compound selected from the foregoing or a combination of two or more compounds are usable.

The above-described organic group (b) is not specifically limited and examples thereof include an alkyl group, an aralkyl group, an alkoxy group, an aryl group, an alkyleneoxy group, an aliphatic hydrocarbon group, and a polyoxyalkylene group, each of which may be substituted. The organic compound preferably plays a role in combining magnetic microparticles and the lipid membrane by allowing the organic group (b) and the lipid membrane to interact with each other via various types of bonding, such as a covalent bond, ionic bond, hydrophobic bond, and hydrogen bond. From such a point of view, the organic group (b) is preferably a hydrophobic, medium to a long chain alkyl group or dissociative group which is capable of interacting with the phospholipid of the lipid membrane. It is therefore desirable to form a side-chain of the compound (A) using a straight chain aliphatic hydrocarbon group having 3 to 30 carbon atoms or a polyalkyleneoxy group of these organic groups (b).

An organic compound which has an organic group (b) at the prescribed carbon atom position of the compound (A) can be prepared by conventionally known methods.

As shown in FIG. 2, organic compound 3 is chemically bonded to magnetic microparticle 2 via at least two binding groups (a) and lipid membrane 4 is formed together with a part of organic group (b), whereby the lipid membrane is strongly bonded. As the magnetic microparticle(s) are bonded to lipid membrane 4 via an organic compound, stability within a human body or during storage is enhanced. Even when subjected to energy exposure in thermotherapy, magnetic vesicular particles are not degraded so that thermotherapy can be efficiently conducted.

Such magnetic microparticles bonded to an organic compound can be made by forming magnetic microparticles in the presence of an organic compound under prescribed conditions.

Specifically, an aqueous solution containing metal ions such as $Fe^{2+}$ is dropwise added to an aqueous solution or dispersion of an organic compound containing at least two functional groups described above and mixed with stirring. It is preferred to control the reaction mixture at a pH of 7 to 10 and a temperature of 3 to 30° C. so as not to impair the activity of the organic compound. The pH can be adjusted using a buffer solution of ammonium acetate, potassium acetate, ammonium chloride, ammonium hydroxide or their mixture. Oxidation is performed under mild conditions to such an extent that aerial oxygen is brought in with stirring, so that the organic compound can be fixed to the ferrite without altering the organic compound or impairing its activity. Magnetic microparticles formed under such mild conditions are homogeneous in composition and uniform in magnetic characteristics. Oxidation may be performed by combining a commonly known method and the use of nitrous acid or hydrogen peroxide with the foregoing method.

When an aqueous solution containing metal ions is dropwise added, the metal ions are adsorbed to a prescribed group of the organic compound and a part of $Fe^{2+}$ ions is oxidized to $Fe^{3+}$ ions to cause formation of a spinel ferrite layer. On the surface of the spinel ferrite layer, hydroxyl groups are formed and further thereon, $Fe^{2+}$ ions are adsorbed and oxidized to form a new spinel ferrite layer. This process is repeated to perform growth of ferrite, whereby magnetic microparticles attached to the organic compound are formed. Various types of ferrites can be made by addition of other metal ions such as $Co^{2+}$, $Ni^{2+}$ and $Zn^{2+}$, in addition to $Fe^{2+}$. The reaction is undergone until magnetic microparticles reach a prescribed size. In this invention, magnetic microparticles can be made by allowing an organic compound having organic group (b) bonded to the basic skeleton of compound (A) to exist in advance. Alternatively, magnetic microparticles can be formed in the presence of only an organic compound having the basic skeleton of compound (A), followed by bonding organic group (b) to compound (A).

It is also preferred that particulate ferrite as a core of the magnetic microparticle is dispersed in an aqueous solution or in a dispersion of an organic compound and according to the foregoing method, a spinel ferrite layer bonded to the organic compound is formed on the surface of the particulate ferrite. The thus prepared magnetic microparticles which are chemically bonded to the organic compound, are comprised of a core of a ferrite having a uniform crystal structure. The use of such magnetic microparticles as a contrast medium in MRI examinations can achieve accurate imaging.

The thus prepared magnetic microparticles to which an organic compound is chemically bonded, are obtained in the form of a dispersion. When using the thus obtained magnetic microparticles in the manufacture of magnetic vesicular particles, it is preferred that the magnetic microparticles are refined by the prescribed method and dispersed in an aqueous medium. As an aqueous medium is employed water such as distilled water, official water for injection or pure water, physiological saline, various buffer solutions and an aqueous salt-containing solution.

In the constitution of the magnetic vesicular particle, magnetic microparticle(s) 2 which are bonded to organic compound 3 are covered with a lipid membrane via the organic compound (as shown in FIGS. 1 and 2). Covering magnetic microparticles with a lipid membrane allows the particles to be dispersed in an aqueous medium and makes it feasible to form a magnetic vesicular particle-containing preparation exhibiting superior dispersion stability. Magnetic microparticles exhibiting a relatively high residual magnetism often cause magnetic coagulation, forming precipitates in medium. The lipid membrane is inherently biocompatible and exhibits enhanced affinity to tissue, and specifically, directionality to hydrophobic tissue is provided to magnetic microparticles. Physiologically active material, medicinally effective material or the like can be advantageously added through designation of lipid membrane constituents, modification of the membrane surface and the like.

Lipid membrane covering magnetic microparticles is generally lipid multi-layer membrane, preferably a multi-layer membrane formed of an amphiphilic molecule having a medium or long chain aliphatic acid residue or a medium or long chain alkyl group and a hydrophilic group. Phospholipid and/or glycolipid are preferably used as such a lipid membrane constituent. A vesicle constituted of lipid bilayer (mainly composed of phospholipid) is generally referred to as "liposome".

Representative examples of a phospholipid include phosphatidylcholine, phosphatidylserine, phosphatidylethanolamine, phosphatidylglycerol, phosphatidylinositol, phosphatidic acid, cardiolipin and sphingomyelin. There are also usable phospholipids derived from plants and animals such as egg yolk or soybeans and their hydrogenation products or hydroxide derivatives, so-called semi-synthetic phospholipids. Fatty acids constituting a phospholipid are not specifically limited, and saturated and unsaturated fatty acids are usable.

Specific examples of neutral phospholipid include dipalmitoylphosphatidylcholine (DPPC), distearoylphosphatidylcholine (DSPC), dimyristoylphosphatidylcholine (DMPC), dioleylphosphatidylcholine (DOPE), dimyristoylphosphatidylethanolamine, dipalmitolphosphatidylethanolamine, and distearoylphosphatidylethanolamine.

In this invention, the lipid membrane preferably forms a liposome. Thus, the magnetic vesicular particles of this invention preferably are liposomes including one or more magnetic microparticles within lipid membrane vesicles. The liposomes preferably exhibit a positive surface charge; in other words, liposome vesicles preferably have the cationic surface. To make the liposome surface charge positive, it is preferred to use, together with the foregoing neutral phospholipid, at least one selected from a cationic phospholipid, a cationic lipid and along chain cationic compound compatible with a phospholipid. Cationic surface charge of liposome membrane enables specific introduction of magnetic vesicular particles contained in the preparation into a negatively charged tumor cell.

Examples of cationic phospholipid include an eater of phosphatidic acid and aminoalcohol, such as an ester of dipalmotoylphosphatidic acid (DPPA) or distearoylphosphatidic acid, and hydroxyethylenediamine. Examples of cationic lipids usable in the invention include 1,2-dioleoyloxy-3-(trimethylammonium)propane (DOTAP), N,N-dioctadecylamidoglycylspermine (DOGS), dimethyloctadecylammonium bromide (DDAB), N-[1-(2,3-dioleyloxy)propyl]-N,N,N-trimethylammonium chloride (DOTMA), 2,3-dioleyloxy-N-[2 (spermine-carboxamido)ethyl]-N,N-dimethyl-1-propaneaminiumtrifluoroacetate (DOSPA) and N-[1-(2,3-dimyristyloxy)propyl]-N,N-dimethyl-N-(2-hydroxyethyl) ammonium bromide (DMRIE). Examples of a long chain cationic compound include at least 10 carbon atoms containing onium salts such as ammonium salt or phosphonium salt.

Examples of glyceroglycolipids include glycerolipids such as digalactosyldiglyceride and digalactosyldiglyceride sulfuric acid ester; sphingoglycolipids such as galactosylceramide, galactosylceramide sulfuric acid ester, lactosylceramide, ganglioside G7, ganglioside G6 and ganglioside G4.

To combine a physiologically active material with the foregoing phospholipid, a functional group capable of being bonded to a physiologically active material may be introduced within a range not deviating from the object of this invention. In addition to the foregoing lipid, other material may optionally be incorporated as a liposome membrane constituent. Examples thereof include glycols such as ethylene glycol and propylene glycol, sterols acting as a membrane stabilizer such as cholesterol, dihydrocholesterol and cholesterol ester. Sterol derivatives are also effective for stabilization of liposome, as described in JP-A No. 5-245357. Of these, cholesterol is specifically preferred.

Sterols are used usually in an amount of from 0.05 to 1.5 parts by weight, preferably from 0.2 to 1 parts by weight and more preferably from 0.3 to 0.8 parts by weight per part by weight of phospholipid. An amount of less than 0.05 parts by weight does not achieve stabilization by the sterol to enhance dispersibility of mixed lipids, while an amount of more than 2 parts by weight inhibits liposome formation or results in unstable formation thereof.

Other additive compounds include, for example, phosphoric acid dialkyl esters as negative-charged material, e.g., diacetyl phosphate, and aliphatic amines as a compound providing a negative charge, such as stearylamine.

In this invention, polyethylene glycol (hereinafter, also denoted simply as PEG) can be used as one constituent for liposome covering magnetic microparticles. Thus, attachment of PEG to the liposome can provide a role as "linkage material" as described later or a new function to the liposome. For example, such a PEG-modified liposome can be expected to have an effect of having a hydrophilic tendency, becoming less recognizable from an immune system or increasing blood stability. Specifically, since lipid components easily accumulate in liver, the use of a liposome containing no PEG or trace amounts of PEG is desired. In the case of integrating other organs, the liposome becomes a state of being stealthy by introduction of a PEG, becoming difficult to be gathered in the liver, therefore, the use of a PEG-modified liposome is recommended. Introduction of a PEG forms a hydration sphere, thereby stabilizing the liposome and enhancing blood retention. Functions can be adjusted by changing a length of oxyethylene units of a PEG and its introducing ratio. Polyethylene glycol having 10 to 3500 (preferably, 100 to 2000) oxyethylene units is preferred as PEG. A PEG is preferably contained in an amount of 0.1% to 30% by weight, and more preferably 1% to 15% by weight, based on the lipid constituting the liposome.

A cholesterol enclosed in the liposome membrane is capable of functioning as an anchor to introduce a polyalkylene oxide. Specifically, cholesterol contained as a liposome membrane constituent in the membrane may optionally be attached to a polyalkylene oxide group via a linker. A short chain alkylene or oxyalkylene group is used as a linker. JP-A No. 9-3093 discloses novel cholesterol derivatives, in which various functional substances can be efficiently fixed at the top of a polyoxyalkylene chain, which can then be employed as a liposome constituent.

PEG-modification of a liposome can be accomplished using commonly known techniques. For example, a polyethylene glycol (PEG) group linked to an anchor compound (e.g., cholesterol, phospholipid) is mixed with a phospholipid as a membrane constituent to form a liposome and the anchor compound may be allowed to be linked to an activated PEG group. Since the PEG group introduced onto the liposome surface is unreactive to "physiologically active material" to be described later, it is difficult to fix the physiologically active material onto the liposome surface. Instead thereof, PEG, the top of which has been chemically modified is bonded to a phospholipid, which is included as a liposome constituent to prepare liposomes.

In place of polyethylene glycol (PEG), commonly known polyalkylene oxide groups may be introduced, which is represented by general formula: -$(AO)_n$—Y where AO is an oxyalkylene group having 2 to 4 carbon atoms, n represents a mean addition molar number and is a positive number of 1 to 2000, and Y is a hydrogen atom, an alkyl group or a functional group. Examples of an oxyalkylene group (represented by "AO") having 2 to 4 carbon atoms include an oxyethylene group, oxypropylene group, oxytrimethylene group, oxytetramethylene group, oxy-1-ethylethylene group and oxy-1,2-dimethylethylene group.

In the foregoing, n is 1 to 2000, preferably, 10 to 500, and more preferably 20 to 200. When n is 2 or more, plural oxyalkylene groups may be the same or differ. In the latter case, differing oxyalkylene groups may be in a random form or in a block form. To provide hydrophilicity to a polyalkylene oxide group, ethylene oxide alone, as AO is preferably addition-polymerized, in which n is preferably 10 or more. In cases when different alkylene oxides are addition-polymerized, it is desirable that at least 20 mol % (preferably at least 50 mol %) of ethylene oxide is addition-polymerized. To provide lipophilicity to an oxyalkylene group, it is preferred to increase the molarity of alkylene oxide(s) other than ethylene oxide. For example, a liposome containing a block copolymer of polyethylene oxide and polypropylene oxide (or polyethylene oxide-block-polypropylene oxide) is a preferred embodiment of this invention.

The designation Y is a hydrogen atom, an alkyl group or a functional group. The alkyl group includes an aliphatic hydrocarbon group having 1 to 5 carbon atoms, which may be branched. The functional group of the foregoing Y is to attach functional material such as sugar, glycoprotein, antibody, lectin and a cell adhesion factor to the top of a polyalkylene oxide group and examples thereof include an amino group, oxycarbonylimidazole group and N-hydroxysuccinimide.

The polyalkylene oxide group plays the role of linkage material, as described later, similarly to polyethylene glycol. The liposome anchoring a polyalkylene oxide chain, to the top of which the foregoing functional material is bonded, not only exhibits effects due to introduction of a polyalkylene oxide group but also gives full play of functions of the functional material, for example, a function as a recognition element, such as directivity to a specific organ and cancerous tissue directivity.

A phospholipid or cholesterol which contains a polyalkylene oxide group can be used alone or in combinations thereof. The content thereof preferably is 0.001 to 50 mol %, more preferably 0.01 to 25 mol %, and still more preferably 0.1 to 10 mol %, based on the total amount of liposome membrane forming components. A content of less than 0.001 mol % results in reduced expected effects.

Introduction of a polyalkylene oxide chain into liposomes can employ commonly known techniques. Thus, an anchor bonding a polyalkylene oxide (e.g., cholesterol, phospholipid) is mixed with phospholipid as a membrane constituent to form liposomes and an activated polyalkylene oxide may be attached to the anchor. This method needs to perform multistage chemical reaction on the liposome membrane surface after completing formation of liposomes. As a result, an introducing amount of an objective physiologically active material is limited to the lower side and contamination with reaction by-products or impurities is caused, causing further problems such as marked damage of the liposome membrane.

As a preferred manufacturing method replacing this, phospholipid polyalkylene oxide derivative is included in advance in phospholipids as raw material to form liposomes.

For examples, JP-A No. 7-165770 proposed polyethylene oxide (PEO) derivatives of a phosphatidylamine and the like, such as distearoylphosphatidyldiethanolamine polyethyleneoxide (DSPE-PEO). Further, JP-A No. 2002-37883 discloses an extremely purified, polyalkylene oxide-modified phospholipid to prepare a water-soluble polymer-modified liposome exhibiting enhanced blood retentivity. It is also disclosed that the use of a polyalkylene oxide-modified phospholipid having a relatively low monoacyl content in the preparation of liposome leads to superior aging stability of liposome dispersions.

Linkage material as a linker allows various physiologically active materials or medicinally effective materials to be bonded in the interior of the magnetic vesicular particle. When a physiologically active material or medicinally effective material having a relatively low molecular weight, as a ligand, is linked to an acceptor, its approach to the ligand is often hindered by steric hindrance due to the magnetic vesicular particle. Such hindrance can be avoided by allowing a linkage material as a spacer having an appropriate length to intervene between the magnetic vesicular particle and a ligand. Preferred examples of a linkage material include a polyethylene glycol chain and a polyalkylene oxide chain, such as ethylene glycol diglycidyl ether (EGDE). A suitable hydrocarbon chain is one which may contain a heteroatom (e.g., oxygen, nitrogen, sulfur, phosphorus). Such a hydrocarbon chain preferably has 2 to 50 carbon atoms (more preferably 3 to 40 carbon atoms, and still more preferably 4 to 30 carbon atoms), which may be substituted by a functional group, an alkyl group or an aryl group. There may be further provided a binding group such as a thio group, epoxy group, amino group, carboxyl group, histidinetagavidine, streptavidin, and biotin. There may be provided oligonucleotide (no. of nucleic acid base: 3-100) or polypeptide (no. of nucleic acid base: 3-50) which is modified with an amino group, carboxyl group or thiol group.

The linkage material may be one member of lipid membrane constituents, as a lipid derivative constituting the lipid membrane.

The magnetic vesicular particles are each bonded to physiologically active material via the linkage material (7) or the organic compound 3, as described above. In the case of liposome-magnetic vesicular particles, physiologically active material may be directly bonded onto the lipid membrane surface of the liposome. Alternatively, physiologically active material is bonded to the organic compound 3 and exists in the interior of the lipid membrane. Examples of physiologically active material include physiologically functional material, additively stabilizing material, medicinally active material, medicinally active chelating material, antitumor-active material, immunopotentiating material, cell fusion material, and gene transfer mediating material. It is also feasible that the foregoing physiologically active material is allowed to bond to magnetic vesicular particles and concentrate selectively to the targeted site through a magnetic operation.

Examples of physiologically functional material include physiological material, such as sugar, glycoprotein, aptamer, antibody, antigen, lectin, cytokine, growth factor, adjustment factor, physiologically active peptide, cell adhesion factor or hormone; and material displaying physiological function, such as metabolic material or an alkaloid.

The antibody may be either a polyclonal antibody or a monoclonal antibody. There are exemplified antibodies attached to various kinds of glycoproteins. Examples thereof include CD44, CD54, CD56 and Fas. Further, an antigen which is expressed specifically in cancer cells and an antibody against tumor-related antigens are also desirable. In this regard, antigens are commonly known, such as MN, HER2, MAGE3, VEGF and CEA.

An antibody against "WTI protein", which does not exist in a normal cell but exists mainly in various kinds of cancer cells or a blood cancer cell, is also cited as a preferred antibody. It is proved that a part of the WTI protein (nine aminoacid-WTI peptides) links to HLA molecule existing on the surface of cancer cell, which becomes a marker of the cancer cell. The foregoing antibody can be prepared by the conventional method, using WTI peptide.

The additively stabilizing material is a material capable of stabilizing a structure of magnetic microparticles which are associated by solvention. Examples thereof include polyvinyl alcohol, polyvinyl pyrrolidone, polyethylene glycol, polyalkylene oxide, dextran, cellulose derivatives, muco-plysaccharide, protein, polypeptide, polyaminoacid, and polynucleotide.

The medicinally active material is a compound exhibiting bioactivity or medicinal effectiveness. Examples thereof include antitumor-active material, anti-infective material, antiviral, antibiotic, anti-inflammatory compound, chemotherapeutic agent, circulatory medicine, alimentary drugs, and neural medicine.

The medicinally active chelating material is material detoxification upon chelate formation or stabilizing action upon chelation. Examples thereof include EDTA, DTPA, cyclin, polycarboxylic acid, polyamino acid, porphyrin, and catecholamine.

The antitumor-active material is material exhibiting tumor-shrinkage effects. Examples thereof include antibiotics, plant alkaloids, alkylation agents, antitumor agents contained in antimetabolite, anti-vascularization medicine and tumor neocrotizing factors. Examples of an anti-vascularization medicine include TNP-470 (AGM-1470, synthesized analog of fungus discharge, named fumagilin, produced by Takeda Chemical Industries Ltd.), and iostatin (Herbert Medical School, Children's Hospital, Surgical Research Lab.), and integlin $\alpha_v\beta_3$ antagonistic drugs (e.g., monoclonal antibody of integlin $\alpha_v\beta_3$, The Scripps Research Institute, LaJolla, Calif.).

The immunopotentiation material is one exhibiting action to enhance activity of immunocytes including lymphocyte and macrophage. Examples thereof include interferon, Krestin, Picibanil, Lentinan, IFA and OK-432.

Cell fusion material is used in a cell fusion operation and promotes cell fusion. Examples thereof include polyalkylene glycol, aryl polyalkylalkylene glycol, arylpolyalkylene glycol, alkylarylpolyalkylene glycol and their derivatives.

The gene transfer mediating material is one functioning as a carrier for gene transfer and examples thereof include polyalkylene glycol (e.g., polyethylene glycol), polyimine (e.g., spermine, spermidine, pentaethylenehexaamine, polyethyleneimine, protamine sulfate), virus vectors and plasmid vectors.

The combination of a photosensitizer of liposomes including phospholipid exhibiting a transition temperature, used for photodynamic therapy and cancer thermotherapy is feasible and enhanced therapeutic effects are expected. A magnetic vesicular particle preparation employing a liposome which links or encloses a photosensitizing material such as porphyrins, 5-aminolevulinic acid, chlorines and phthalocyanine, is given to a patient, and after an elapse of time and when heated from the outside of body, local thermotherapy is conducted using microwaves or electromagnetic waves.

The preparation containing magnetic vesicular particles, according to this invention, may optionally contain, as auxiliary agents, a pharmaceutically allowable buffering agent, stabilizer, antioxidant such as α-tocopherol, viscosity-adjusting agents or chelating agents. These are optimally employed prevent oxidation reduction reaction or alteration such as coagulation or precipitation. One feature of the preparation of this invention is that any organic solvent is not substantially contained in the included lipid membrane or in the internal water phase.

Manufacturing methods of the preparation containing magnetic vesicular particles of this invention are not specifically limited if the magnetic microparticle surface bonded to the afore-mentioned organic compound can be covered with lipid membrane. The preparation can also be manufactured employing a conventional shaking method. However, in conventional methods, the phospholipid needs to be dissolved in chlorinated solvents and unremoved chlorinated solvents are feared to remain in the preparation, often causing problems with respect to safety for the human body. On the contrary, the preparation containing magnetic vesicular particles of this invention can be manufactured substantially without using organic solvents such as chlorinated solvents. Thus, the preparation can be made by the method using supercritical carbon dioxide. The expression, substantially without using organic solvents means that the upper limit of the residual organic solvent concentration of the preparation is 10 μg/L. In the following, supercritical carbon dioxide includes subcritical carbon dioxide.

A preferred method of manufacturing the preparation containing magnetic vesicular particles comprises:

the first step in which the lipid membrane constituent described above and liquefied carbon dioxide are mixed within a pressure vessel, after which applying heat and pressure to the interior of the vessel forms supercritical carbon dioxide, and while mixing the lipid membrane constituents and the supercritical carbon dioxide, a dispersion of magnetic microparticles chemically bonded to an organic compound is further added thereto and mixed, and the second step in which after obtaining the mixture in the foregoing step, the interior of the pressure vessel is evacuated to discharge carbon dioxide, thereby covering (or enclosing) the magnetic microparticles with lipid membrane to form magnetic vesicular particles, resulting in an aqueous dispersion of magnetic vesicular particles.

The foregoing method preferably further comprises the third step in which the aqueous dispersion of magnetic vesicular particles is subjected to filtration using a filter membrane of a pore size of 100 to 1000 nm.

The respective steps will be further described as below.

In the first stage, while mixing lipid membrane constituents and liquefied carbon dioxide in a pressure vessel, the pressure and the temperature in the interior of the vessel are adjusted so that the carbon dioxide becomes supercritical, and the lipid membrane constituents and the supercritical carbon dioxide are mixed.

In the manufacturing method of this invention, the pressure suitable for carbon dioxide in a supercritical state is from 50 to 500 kg/cm$^2$ but preferably from 100 to 400 kg/cm$^2$. The temperature suitable for the supercritical carbon dioxide is from 25 to 200° C., preferably from 31 to 100° C., and more preferably from 35 to 80° C. It is preferred to maintain the supercritical state by the combination of temperature and pressure within the foregoing range. Stirring conditions are not specifically limited and suitable ones are appropriately chosen.

Subsequently, while mixing lipid membrane constituents and supercritical carbon dioxide, a dispersion of magnetic microparticles which are chemically bonded to an organic compound, is further added thereto and mixed. The dispersion may be added all at once or intermittently with maintaining the supercritical state.

In the second stage, after obtaining the mixture in the foregoing step, the interior of the pressure vessel is evacuated and carbon dioxide is discharged, whereby an aqueous dispersion of magnetic vesicular particles (or vesicles) in which the magnetic microparticles are covered with lipid membrane.

The organic compound bonded to the magnetic microparticles has the afore-mentioned organic group (b), a part of which is enclosed in the formation of lipid membrane and connected to the lipid membrane. Thus, the magnetic microparticles and the lipid membrane are tightly bonded via the organic compound. Accordingly, stability within the human body or during storage is enhanced and for instance, the magnetic vesicular particles are not degraded even when subjected to energy exposure in thermotherapy, performing efficient thermotherapy. In this stage, one or plural magnetic microparticles are enclosed (or covered) with lipid membrane, whereby an aqueous dispersion of magnetic vesicular particles is obtained.

In the third stage, the aqueous dispersion of magnetic vesicular particles, obtained in the second stage, is filtered using a filter membrane having a pore size of 100 to 1000 nm. Specifically, the aqueous dispersion is passed through an extruder installed with a filter having a pore of 100 to 1000 nm, whereby 100-150 nm magnetic vesicular particles can be efficiently made. Thus, adjustment of size and size-distribution of the magnetic vesicular particles can achieve the objective effects of the preparation containing magnetic vesicular particles.

The magnetic vesicular particles of this invention have such an advantage that the dose of magnetic microparticles, in other words, the dosage of lipid can be reduced, compared to magnetic vesicular particles comprised of multilamellar vesicles (also denoted simply as MLV). In the conventional manufacturing method of liposomes, MLV of various sizes and forms often exist in a considerable quantity. Accordingly, an operation such as ultrasonic exposure or passing through a filter having a prescribed pore size a few times was needed to enhance the proportion of unilamellar or several lamellar liposomes. On the contrary, in the method of this invention in which liposomes are formed using supercritical carbon dioxide, liposomes of unilamellar or several-lamellar vesicles can efficiently be produced, whereby an enhanced rate of enclosing a drug in the liposomes can be achieved.

The thus obtained aqueous dispersion of magnetic vesicular particles is filtered using the filtration membrane described above to make a preparation containing magnetic vesicular particles, which may be further subjected to centrifugal separation or ultrafiltration to separate an aqueous medium from the dispersion, whereby concentrated dispersion is obtained.

The preparation containing magnetic vesicular particles of this invention are usable as a medical preparation, i.e., as an imaging agent for used in examination or diagnosis and also as a therapeutic agent. Specifically, it can be used as a contrast medium such as a radiographic contrast medium, a contrast medium for use in MRI (nuclear magnetic resonance imaging method) or an ultrasonic contrast medium, and as a therapeutic agent for cancer or the like, preferably, a therapeutic agent for use in thermotherapy.

The radiographic contrast medium is given to a lumen region such as a vascular tract, a ureter or a uterine tube to be used for examination of a form or stenosis of the lumen. However, conventionally used compounds are promptly discharged from the lumen region without interacting with tissue or disease regions, which is not useful for detailed examination of the tissue or diseased region, specifically such as cancerous tissue. Therefore, an X-ray contrast medium has been desired which can be selectively accumulated in/or onto the targeted tissue or diseased region, thereby giving an image which can be distinguished with clear contrast from the circumference or other regions.

Examination and diagnosis in MRI produce no problem due to radiation exposure and any sectional image of organism can be obtained non-invasively, which is a rapidly spreading image diagnosis technology. To obtain clear images by enhancing contrast, a contrast medium capable of varying the proton relaxation time is employed in MRI. As a contrast medium for use in MRI, gadolinium-diethylenetriaminepentaacetic acid (hereinafter, also denoted simply as Gd-DTPA) is only one contrast-enhancing agent at the present time. The Gd-DTPA contrast medium which has been introduced into a human body is transferred to tissue by the circulating bloodstream. However, the contrast medium itself has no capability of discriminating tissue.

Ultrasonic image diagnostics usually allow ultrasonic having a frequency of 1 to 10 MHz to permeate into the interior of the body of an examinee via a converter, on the basis of ultrasonic waves interacting with the interface of body tissue or body liquid (or humor). An image formed by ultrasonic signals is derived from differential reflection/absorption of ultrasonic in the interface. An ultrasonic contrast medium of microcapsules enclosing gas or bubbles is used in this diagnosis method. However, the amount of enclosed gas or bubbles is not always so large, depending on other factors. Accordingly, a sufficient contrast effect is achieved only by a large amount of dose.

The magnetic vesicular particles which have been introduced into the body as a contrast medium for use in radiography or MRI or as a ultrasonic contrast medium can be selectively accumulated in/or onto the targeted tissue or diseased region, resulting in an image which can be distinguished with clear contrast from the circumference or other regions. Thus, the magnetic vesicular particles of this invention can be selectively accumulated in/or onto the targeted tissue or disease region through their grain sizes or surface charge and can provide the capability of discriminating tissue via physiologically active material attached to the lipid membrane surface. Furthermore, imaging of tumorous tissue can be effectively realized, due to the fact that the ultrasonic propagation in magnetic microparticles is faster than that in a living body (water). Thus, employing such characteristics, the preparation containing magnetic vesicular particles can be used suitably as a contrast medium for use in radiography or MRI, or a ultrasonic contrast medium.

Specifically, within not less than 1 min. and not more than 48 hr., preferably not less than 30 min. and not more than 36 hr. after the preparation containing magnetic vesicular particles of this invention is given into a vein of an examinee, a scan is conducted in a ultrasonic imaging diagnosis apparatus, a nuclear magnetic resonance imaging diagnosis apparatus or an X-ray imaging diagnosis apparatus, thereby achieving enhanced detection of tumorous tissue. The preparation containing magnetic vesicular particles may be directly injected near tumorous tissue of an examinee; within not less than 0.5 min. and not more than 36 hr., preferably not less than 10 min. and not more than 24 hr. after the preparation containing magnetic vesicular particles of this invention is dosed into a vein of an examinee, scan is conducted in a ultrasonic imaging diagnosis apparatus, a nuclear magnetic resonance imaging diagnosis apparatus or an X-ray imaging diagnosis apparatus, thereby achieving enhanced detection of tumorous tissue.

The magnetic vesicular particle-containing preparation of this invention is usable as an imaging agent for examination and diagnosis. Since the preparation bonds or encloses a physiologically active material, medicinally effective material or an antitumor agent inside or outside the lipid membrane, the preparation is also usable as a therapeutic agent for various diseases. The magnetic vesicular particles are accumulated selectively onto focus such as a diseased region or tumorous tissue. Action of a physiologically active material or medicinally effective material is effectively displayed, thereby reducing adverse effects.

Specific application is exemplified below, but application of the preparation of this invention is not limited to this.

Thermotherapy for cancer as well as laser therapy or photodynamic therapy belongs to a category of a non-invasive treatment for cancer. Such cancer thermotherapy, which is a treatment having specific characteristics and superior faces, has not necessarily been adopted in treatment sites for cancer. Thermotherapy has not been employed alone but is employed in combination with radiation or an anticancer drug for enhancing effects of the radiation or anticancer drugs. There may be cited various reasons therefor. Such therapy has not always achieved superior results to other types of treatment. There may be no reason for this therapy to be replaced by other treatments. There is still room for improvement of members, drugs and devices.

The present target of this therapy is locally progressive cancer and recurring cancer which are difficult to be cured in usual treatments. Thermotherapy include warming the whole body (general thermotherapy) and warming the cancer site or its vicinity (local thermotherapy). In general, local thermotherapy is mainly conducted using a device employing microwaves, electromagnetic waves (alternating magnetic fields) or ultrasonic waves to perform localized warming. A system of warming from the outside of the body is most frequently conducted. There is also attempted the method of inserting an instrument into a lumen such as esophagus, rectum, uterus or bile duct and a method inserting several electrode needles into cancerous tissue to perform warming. Effects on cancer are achieved at 41° C. or more, and preferably 42.5° C. or more. Cancer near the body surface can readily be warmed to an intended temperature. Cancer localized deep in the body is often difficult to be sufficiently warmed due to hindrance of fat, air or bone. Introducing the magnetic vesicular particle-containing preparation of this invention into a body to be used as a heating element for thermotherapy can achieve effective therapeutic effects on cancerous tissue in the interior of the body, scattered cancer cells, or minute initial cancer cells.

Specifically, when an examinee is subjected to energy exposure within not less than 1 min. and not more than 48 hr. (preferably, not less than 30 min. and not more than 36 hr.) after the start of dosing of the magnetic vesicular particle-containing preparation of this invention into the vein of the examinee, the temperature of cancerous tissue near the magnetic vesicular particles is raised and a therapeutic treatment is performed without adverse effect to normal cells. The preparation may also be directly injected near tumorous tissue of the examinee. Exposure of an examinee to energy within not less than 0.5 min. and not more than 36 hr. (preferably, not less than 10 min. and not more than 24 hr.) after the start of injection raises the temperature of tumorous tissue near magnetic vesicular particles. Preferred examples of energy exposure include exposure to an alternating magnetic field and exposure to ultrasonic waves. The exposure to an alternating magnetic field is conducted preferably at a frequency of 25 to 500 kHz.

Preferred embodiments of a diagnostic therapeutic system using the magnetic vesicular particle-containing preparation of this invention will be now be described with reference to a drawing. The embodiment shown in the drawing is one of the embodiments of this invention, but the invention is by no means limited to this.

Figure 3:
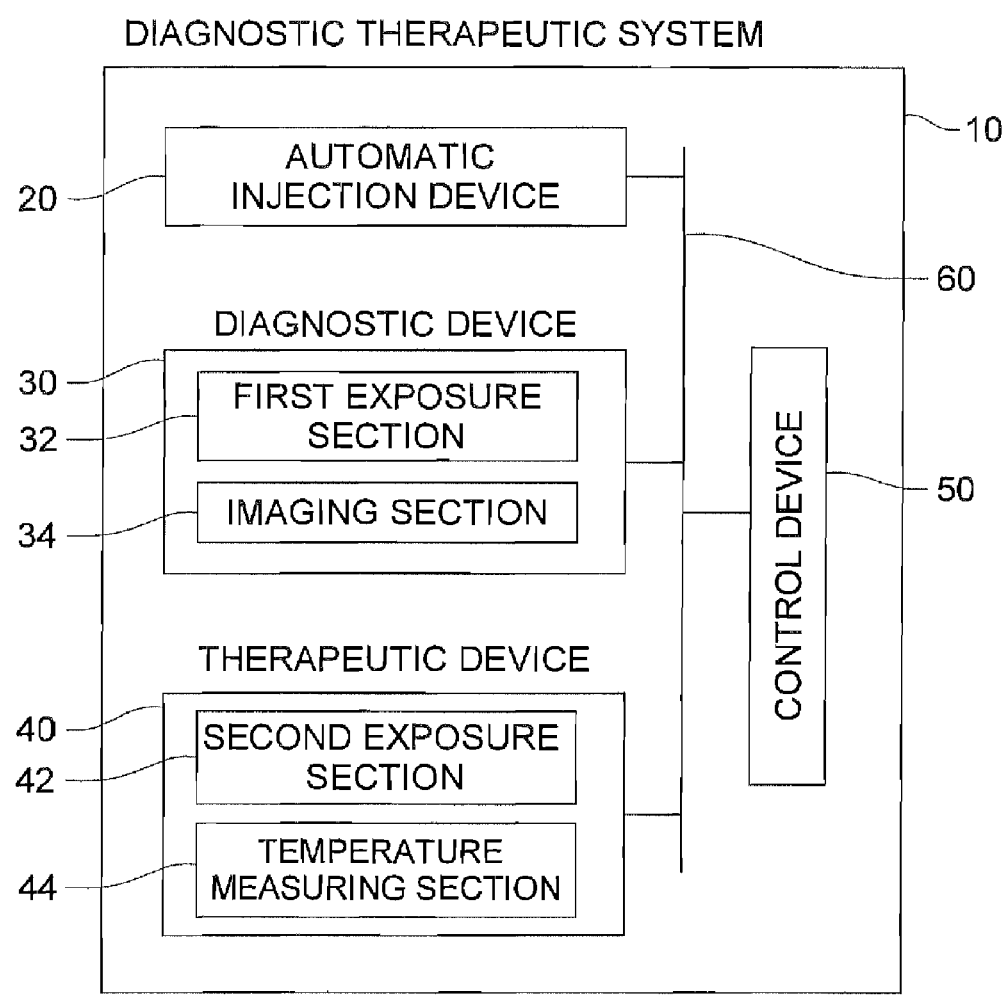
FIG. 3 illustrates an embodiment of a diagnostic therapeutic system employing a preparation containing magnetic vesicular particles.

As shown in FIG. 3, diagnostic therapeutic system 10 relating to this invention comprises:

automatic injection device 20 for automatically giving a preparation containing magnetic vesicular particles of this invention to an examinee, diagnostic device 30 provided with first exposure section 32 for subjecting the preparation-given examinee to exposure to an ultrasonic wave, an electromagnetic wave or an X-ray, and imaging section 34 for scanning a tumor site in which the magnetic vesicular particles are accumulated under the exposure to an ultrasonic wave, an electromagnetic wave or an X-ray, therapeutic device 40 provided with second exposure section 42 of subjecting the tumor site in which the magnetic vesicular particles are accumulated to exposure to an alternating magnetic field or an ultrasonic wave, and temperature measuring section 44 for measuring a temperature of the tumor site and that of a normal site near the tumor site under the exposure to an alternating magnetic field or an ultrasonic, and control device 50 which is connected to the automatic injection device 20, the diagnostic apparatus 30 and the therapeutic apparatus 40 through network 60 and which controls an operation of each of these apparatuses and conducts control among these apparatuses.

As the automatic injection device 20 are usable conventionally known ones. A radiographic imaging diagnostic device, a nuclear magnetic resonance imaging diagnostic device or an ultrasonic imaging diagnostic device is usable as the diagnostic device 30. A focused ultrasonic heating device or an alternating magnetic field heating device is usable as the therapeutic device 40. Preferably, the automatic injection device 20, the diagnostic device 30 and the therapeutic device 40 are integrated so as to concurrently perform diagnosis and therapy.

Any apparatus which is provided with a control section (CPU), an operating section such as a keyboard and a mouse and a display section such as a memory and a display, is applicable as the foregoing control device 50, and examples thereof includes a computer. The network 60 may be connected through information communication network, such as an internet, LAN (Local Area Network) or WAN (Wide Area Network). Connection of terminals of these is unconcerned with being with wire or wireless.

The diagnostic therapeutic system 10 preferably has a patient information database. The control device 50 can access the database according to its need to obtain information of an examinee, whereby an approximate position of the tumor site and constitution or health conditions of the examinee can be confirmed in advance.

In the diagnostic therapeutic system 10, first, the automatic injection device 20 automatically gives a preparation containing magnetic vesicular particles to a patient whose tumor site is to be examined and treated. Specifically, when a patient is taken in the diagnostic therapeutic system, first of all, information for specifying the patient is obtained from an IC tag or a biometric certification such as finger prints or an iris of the patient. The control device 50 accesses the database based on such information to specify the patient. Then, the control device determines the kind or dose of the preparation containing magnetic vesicular particles from the data (chart) of the patient and transmits the automatic injection device 20.

The automatic injection device 20 receives the data such as kind or dose from the control device 50 and then doses a preparation containing magnetic vesicular particles to the patient according to predetermined items. When completing the dose of the preparation, the automatic injection device 20 transmits a signal of completion of the dose to the control device 50. Subsequently, the control device 50 transmits a signal of starting diagnosis of the tumor site to the diagnostic device 30.

The diagnostic device 30 having received the signal allows the first exposure section 32 to expose the patient to ultrasonic, electromagnetic wave or X-ray and further allows the imaging section 34 to scan the tumor site in which magnetic vesicular particles are accumulated. The image data obtained by scanning in the imaging section 34 is transmitted the control device 50. The control device 50 confirms contrast of the image based on the previously inputted data to specify the tumor site in which magnetic vesicular particles are accumulated. Preferably, the system 10 is provided with a display section such as a monitor to artificially confirm the image scanned in the imaging section 34.

The control device 50, which has specified the tumor site, allows the data regarding the position of the tumor site to be contained in the database of the patient and further transmits the information regarding the position of the tumor site to the therapeutic device 40. The therapeutic device 40 which has received the data regarding the position of the tumor site, allows the second exposure section 42 to expose the patient to an alternating magnetic field or an ultrasonic and further allows the temperature measuring section 44 to measure the temperature of the tumor site and the vicinity thereof. In the temperature measurement of the temperature measuring section 44, the temperature in vivo is non-invasively measured without embedding a sensor, applying temperature variation being represented as variation of resonance frequency. Preferably, the temperature measuring section 44 conducts temperature measurement which calculates the temperature from a vertical relaxation time by a signal intensity method, a proton chemical shift by a phase method or a diffusion coefficient by a diffusion image method, each of which uses a nuclear magnetic resonance imaging apparatus, or from values obtained in microwave radiometry using plural frequencies.

When the control device 50 judges that the tumor site is too small to perform an effective treatment or judges that a treatment is to be conducted with confirming the tumor site, the control device 50 controls the first exposure section 32 to allow the tumor site to be exposed to an ultrasonic wave, electromagnetic wave or X-ray and the second exposure section 42 to allow the tumor site to be exposed to an alternating magnetic field or ultrasonic to perform therapy, while scanning, by the imaging section, the tumor site in which magnetic vesicular particles are accumulated.

The temperature measuring section 44, which has measured the temperature of the tumor site and a normal site near the tumor site, successively sends the results thereof to the control device 50. The control device 50, which has received the measurement results and confirmed that the tumor site has been raised to a prescribed temperature (e.g., 42° C.), sends the second exposure section 42 an order of stopping the exposure to an alternating magnetic field or an ultrasonic wave. After reaching the prescribed temperature, the control device may control the second exposure section 42 so as to continue exposure to an alternating magnetic field or an ultrasonic for a given period of time. In cases when the tumor site has not reached a prescribed temperature and the normal site near the tumor site has reached the prescribed temperature, the control device 50 sends the second exposure section 42 an order of stopping the exposure to an alternating magnetic field or an ultrasonic.

As described above, the diagnostic therapeutic system can perform confirmation of a tumor site to the therapy thereof in a single system. Thus, diagnosis and therapy, which were conventionally conducted separately, are concurrently performed and lightens the burden on a patient, performing diagnosis and therapy effectively and efficiently.

There has been described the diagnostic therapeutic system of this invention but the invention is not limited thereto, and various changes and modifications can be made therein without departing from the object of this invention.

EXAMPLES

The present invention will be further described with reference to specific examples but the invention is by no means limited to these.

Organic Compound A

Organic compounds A which is to be added in the course of manufacturing magnetic microparticles, is prepared in the manner described below.

A hydroxyl group of malic acid and that of tetramethyleneglycol monomethyl ether were reacted through hexamethylene diisocyanate to form tetramethyleneglycol monomethyl ether-modified malic acid (A-1). Similarly to the foregoing, hexamethyleneglycol monomethyl ether-modified malic acid (A-2) and decaethyleneglycol monomethyl ether-modified malic acid (A-3) were prepared. An amino group of asparagic acid and that of tetramethyleneglycol monomethyl ether were reacted through hexamethylene diisocyanate to form tetramethyleneglycol monomethyl ether-modified asparagic acid (A-4).

A hydroxyl group of malic acid was reacted with octanoic acid chloride to form octanoic acid-modified malic acid (A-5). An amino group of asparagic acid was reacted with stearic acid chloride to form stearic acid-modified asparagic acid (A-6).

The thus prepared organic compound A is as follows:
- A-1: tetramethyleneglycol monomethyl ether-modified malic acid,
- A-2: hexamethyleneglycol monomethyl ether-modified malic acid,
- A-3: decaethyleneglycol monomethyl ether-modified malic acid,
- A-4: tetramethyleneglycol monomethyl ether-modified asparagic acid,
- A-5: octanoic acid-modified malic acid,
- A-6: stearic acid-modified asparagic acid.

Formation of Magnetic Microparticles

Formation Method 1

A 0.1 mol/L ferrous chloride solution and a 0.1 mol/L ferric chloride solution were mixed with each other at equal volumes to form solution (1). A 28 wt % aqueous ammonia was diluted to 0.01 wt % with distilled water to obtain solution (2). An aqueous solution containing organic compound A at a concentration of 1 mmol/L, as shown in Table 1 was prepared. This solution was adjusted to a pH of 8.4-10.0, using a 1 mol/L buffer solution composed of ammonium hydroxide and ammonium chloride to obtain solution (3).

10.00 ml of the solution (3) was stirred while maintaining a temperature at 5° C. and blowing air. The solution (1) and solution (2), each of 5.0 ml were dropwise added into the solution (3). The addition rate was adjusted so that the pH was maintained within a range from 7.0 to 8.5 with confirming the pH with a pH-meter and the temperature was maintained at 5 to 15° C. with monitoring the temperature by a temperature controller. After completion of addition, stirring was continued for 1 hr., then, magnetic microparticles were separated through magnetic separation and washed well with distilled water to obtain magnetic microparticles which were chemically bonded to organic compound A having at least two specific bonding groups. The stirring speed and the addition rate of the respective solutions (1) and (2) were controlled so that the pH and the temperature were maintained with the foregoing range. Magnetic ferrite particles having an average particle size (r), as shown in Table 1, were thus formed. Using a transmission electron microscope, magnetic microparticles were observed to determine their particle sizes and the average value of 20 particles was defined as the particle size (r).

Formation Method 2

Similarly to the foregoing formation method 1, solutions (1) and (2) were prepared. An aqueous solution containing an organic compound A at a concentration of 1 mmol/L, as shown in Table 1 was prepared. This solution was adjusted to a pH of 8.4-10.0, using a 1 mol/L buffer solution composed of ammonium hydroxide and ammonium chloride to obtain solution (3). The aqueous solution described above was adjusted to a pH of 8.4-10.0 to obtain solution (4).

5.00 ml of the solution (4) was stirred while maintaining a temperature of 5° C. and blowing air thereinto. The solution (1) and solution (2), at 2.5 ml of each, were dropwise added to the solution (4) to prepare solution (5). Subsequently, 5.0 ml of the solution (3) was added to the solution (5) and further thereto, solutions (1) and (2), 2.5 ml of each were added dropwise. The addition rate was adjusted so that a pH of 7.0 to 8.5 was maintained with confirming the pH using a pH-meter and the temperature was maintained at 5 to 15° C. with monitoring the temperature by a temperature controller. After completion of addition, stirring was continued for 1 hr., then, magnetic microparticles were separated through magnetic separation and well washed with distilled water to obtain magnetic microparticles which were chemically bonded to an organic compound A having at least two specific groups. The stirring speed and the addition rate of the respective solutions (1) and (2) were controlled so that the pH and the temperature of the solution (4) or (5) were maintained with the foregoing range. Magnetic ferrite particles having a particle size, as shown in Table 1, were thus formed. Using a transmission electron microscope, magnetic microparticles at the time when the solution (5) was prepared were observed to determine their particle sizes and an average value of 20 particles was defined as particle size (r1). Similarly, finally formed magnetic microparticles were observed and the average value of 20 particles was defined as particle size (r).

Formation Method 3

Similarly to the foregoing formation method 1, solutions (1) and (2) were prepared. An aqueous solution containing organic compound B at a concentration of 1 mmol/L, as shown in Table 1 was prepared. This solution was adjusted to a pH of 8.4-10.0, using a 1 mol/L buffer solution composed of ammonium hydroxide and ammonium chloride to obtain solution (3). Subsequently, similarly to the foregoing method 1, solutions were mixed to obtain magnetic microparticles which were chemically bonded to organic compound B having at least two specific groups.

The magnetic microparticles were dried, placed in hexane and dispersed using an ultrasonic dispersing machine. To the hexane dispersion of the magnetic microparticles, acid chloride organic compound C) shown in Table 1, which was diluted with hexane to 1 wt %, was added to allow the organic compound B which was chemically bonded to the magnetic microparticles and the compound C to react with each other. Subsequently, isopropyl alcohol was added thereto to esterify excess organic compound C, thereafter, magnetic microparticles were separated through magnetic separation and well washed with acetone and distilled water to obtain magnetic microparticles which were chemically bonded to organic compound B and the organic compound was further bonded to organic compound C. The stirring speed and the adding rate of the respective solutions (1) and (2) were controlled so that the pH and the temperature were maintained within the foregoing range. Magnetic ferrite particles having a particle size (r), as shown in Table 1, were thus formed. The particle size (r) was determined similarly to the method 1.

Formation Method 4

Solutions (1), (2) and (4) were each prepared similarly to the formation method 2, and solution (3) was prepared similarly to the formation method 3, except for the use of organic compound B. Subsequently, magnetic microparticles which were chemically bonded to organic compound B having at least two specific groups, were prepared similarly to the method 2.

After the magnetic microparticles were dried, organic compound B, which was chemically bonded to magnetic microparticles and compound C were reacted in hexane similarly to the formation method 3. Subsequently, isopropyl alcohol was added thereto to esterify excess organic compound C, thereafter, magnetic microparticles were separated through magnetic separation and well washed with acetone and distilled water to obtain magnetic microparticles which were chemically bonded to organic compound B and the organic compound is further bonded to organic compound C.

The stirring speed and the addition rate of the respective solutions (1) and (2) were controlled so that the pH and the temperature of the solutions (4) and (5) were maintained within the foregoing range. Magnetic ferrite particles having particle sizes, as shown in Table 1, were thus formed. Particle sizes (r1) and (r) were each determined similarly to the formation method 2.

Magnetic microparticles for comparison in which an organic compound was not added in the course of magnetic microparticle formation, were prepared similarly to the methods 1 to 4.

Formation Method 5

Comparative magnetic microparticles onto the surface of which stearic acid was adhered, were prepared in the following manner. Thus, 1.67 g of ferrous sulfate heptahydrate [Fe(II) SO$_4$.7H$_2$O] was placed into a sample bottle and dissolved in 8 ml of nitrogen-substituted water. Then, 1 ml of an aqueous sodium nitrite solution (having a concentration of 0.07 g/ml) was added, 5 ml of 28 wt % aqueous ammonia was further added and stirred under an atmosphere of nitrogen, while maintaining a temperature at 40° C. Formed magnetic microparticles were taken out, placed into a vessel and allowed to stand at 40° C. for 30 min. The magnetic microparticles were washed twice with 25 ml of 1.4 wt % aqueous ammonia. Thereafter, the magnetic microparticles were subjected to centrifugation for 5 min. using a centrifugal separator at a rotation speed of 3,000 rpm. The precipitated magnetic microparticles were placed in a sample bottle. Subsequently, after heating at 110° C. for 5 min., 0.14 g of stearic acid was added and heated at 110° C., and stirring and being allowed to stand were repeated for 15 min. Then, 10 ml of degassed water was added and allowed to stand at 14° C. overnight and subjected to dialysis using pure water to obtain magnetic microparticles to which stearic acid was chemically bonded. The particle size (r) was determined similarly to the foregoing formation method 1.

TABLE 1

| Magnetic Microparticle No. | Microparticle Formation Method | Organic Compound A | Organic Compound B | Organic Compound C | Particle Size | |
|---|---|---|---|---|---|---|
| | | | | | r (nm) | r1 (nm) |
| 1 | 1 | A-1 | — | — | 15 | |
| 2 | 1 | A-2 | — | — | 15 | |
| 3 | 1 | A-3 | — | — | 15 | |
| 4 | 1 | A-3 | — | — | 20 | |
| 5 | 1 | A-4 | — | — | 15 | |
| 6 | 1 | A-5 | — | — | 15 | |
| 7 | 1 | A-6 | — | — | 5 | |
| 8 | 1 | A-6 | — | — | 10 | |
| 9 | 1 | A-6 | — | — | 20 | |
| 10 | 1 | A-6 | — | — | 30 | |
| 11 | 2 | A-2 | — | — | 15 | 12 |
| 12 | 2 | A-4 | — | — | 15 | 12 |
| 13 | 2 | A-6 | — | — | 1 | 0.8 |
| 14 | 2 | A-6 | — | — | 2.5 | 2 |
| 15 | 2 | A-6 | — | — | 5 | 4 |
| 16 | 2 | A-6 | — | — | 10 | 8 |
| 17 | 2 | A-6 | — | — | 20 | 16 |
| 18 | 3 | — | B-1 | C-2 | 10 | |
| 19 | 3 | — | B-4 | C-2 | 10 | |
| 20 | 3 | — | B-5 | C-2 | 10 | |
| 21 | 4 | — | B-1 | C-1 | 10 | 8 |
| 22 | 4 | — | B-4 | C-1 | 10 | 8 |
| 23 | 4 | — | B-5 | C-1 | 10 | 8 |
| 24 | 4 | — | B-1 | C-2 | 10 | 8 |
| 25 | 4 | — | B-2 | C-2 | 10 | 8 |
| 26 | 4 | — | B-3 | C-2 | 10 | 8 |
| 27 | 4 | — | B-4 | C-2 | 10 | 8 |
| 28 | 4 | — | B-5 | C-2 | 10 | 8 |
| 29 | 1 | — | — | — | 10 | |
| 30 | 1 | — | — | — | 20 | |
| 31 | 5 | — | — | — | 10 | |
| 32 | 5 | — | — | — | 20 | |

Examples 1-44 and Comparative Examples 1-10

Manufacturing Method 1

Using magnetic microparticles, as shown in Table 2, magnetic vesicular particles were prepared in the following manner. In a 10 ml eggplant type flask, 1.5 mg of dipalmitoylphosphatidylcholine (DPPC), 8.5 mg of phosphatidylethanolamine and 20 mg of phosphatidylcholine were dissolved in 2.0 ml of chloroform to form a homogeneous solution. Thereafter, solvents in the solution were removed under reduced pressure and dried overnight in a desiccator to form a DPPC film in the flask.

Subsequently, distilled water was added to the magnetic microparticles described in Table 2 to form a slurry suspension containing the magnetic microparticles at a concentration of 10 µg/µl. The slurry suspension was added into the flask, at 0.5-6.0 µm and further thereto was added 0.4 ml of a phosphoric acid-buffered physiological saline of a 10-fold concentration was added. The thus formed mixture was stirred by repeating ultrasonic stirring over 60 sec. and then pausing over 30 sec. for a period of 60 min. After completion of ultrasonic stirring, the mixture was subjected to centrifugal separation for 15 min. using a centrifugal separator at a rotation speed of 3,300 rpm. The obtained supernatant was further subjected to centrifugation at a rotation speed of 7,500 rpm for 50 min., whereby lipid membrane-magnetic vesicular particles having a grain size (R) shown in Table 2 were obtained as precipitates. The grain size of the magnetic vesicular particles was observed using a transmission electron microscope. The grain size (R) is an averaged value of 20 magnetic vesicular particles.

Manufacturing Method 2

In a 10 ml eggplant type flask, dimethyloctadecylammonium bromide, dioleylphosphatidylcholine (DOPE) and C-2 ceramide at a ratio of 1:1:2 (in a total amount of 2 ml) were dissolved in 2.0 ml of chloroform to form a homogeneous solution. Thereafter, solvents of the solution were removed under reduced pressure and dried overnight in a desiccator to form a DPPC film in the flask.

Subsequently, distilled water was added to the magnetic microparticles described in Table 2 to form a slurry suspension containing magnetic microparticles at a concentration of 10 µg/µl. The slurry suspension was added into the flask, within an amount of 0.5 to 6.0 µm and further thereto, a phosphoric acid-buffered physiological saline at a 10-fold concentration was added in an amount of 1/10 of the volume of the slurry suspension of magnetic microparticles. The thus formed mixture was stirred by repeating ultrasonic stirring over 60 sec. and pausing over 30 sec. for a period of 60 min. After completion of ultrasonic stirring, the mixture was subjected to centrifugal separation for 15 min. using a centrifugal separator at a rotation speed of 3,300 rpm. The obtained supernatant was further subjected to centrifugation at a rotation speed of 7,500 rpm for 50 min., whereby phospholipid membrane-magnetic vesicular particles having a grain size (R) shown in Table 2 were obtained as precipitates. The grain size (R) of the phospholipid membrane-magnetic vesicular particles was determined similarly to the foregoing manufacturing method of the lipid membrane-magnetic vesicular particles.

Manufacturing Method 3

A mixture of 40 mg of DPPC, 1.2 mg of a block copolymer of polyethyleneoxide and polypropyleneoxide (pluronic F-88, produced by ADEKA Co., Ltd.) and 900 mg of ethanol was placed into a stainless steel autoclave and the interior of the autoclave was heated to 60° C., then, 13 g of liquid carbon dioxide was added thereto. The pressure within the autoclave was increased from 50 kg/cm$^2$ to 200 kg/cm$^2$ and DPPC was allowed to be dissolved in the supercritical carbon dioxide, while stirring within the autoclave. Subsequently, physiological saline was added to the magnetic microparticles described in Table 2 to form a slurry suspension containing magnetic microparticles at a concentration of 10 µg/µl.

While stirring the supercritical carbon dioxide solution, the foregoing slurry suspension was continuously added thereto within a range of 0.5 to 6.0 ml. The interior of the autoclave was then evacuated to discharge the carbon dioxide.

The mixture was subjected to centrifugal separation for 15 min. using a centrifugal separator at a rotation speed of 3,300 rpm. The obtained supernatant was further subjected to centrifugation at a rotation speed of 7,500 rpm for 50 min., whereby phospholipid membrane-magnetic vesicular particles having a grain size (R) shown in Table 2 were obtained as precipitates. The grain size (R) of the phospholipid membrane-magnetic vesicular particles was determined similarly to the foregoing manufacturing method of the lipid membrane-magnetic vesicular particles.

Manufacturing Method 4

Dimethyloctadecylammonium bromide, dioleylphosphatidylcholine (DOPE) and C-2 ceramide were mixed at a ratio of 1:1:2 (in a total amount of 2 ml). The obtained mixture and 900 mg of ethanol was placed into a stainless steel autoclave and the interior of the autoclave was heated to 60° C., then, 13 g of liquid carbon dioxide was added thereto. The pressure within the autoclave was increased from 50 kg/cm$^2$ to 200 kg/cm$^2$ and DOPE was allowed to be dissolved in the supercritical carbon dioxide, while stirring within the autoclave. Subsequently, physiological saline was added to the magnetic microparticles described in Table 2 to form a slurry suspension containing magnetic microparticles at a concentration of 10 µg/µl.

While stirring supercritical carbon dioxide solution, the foregoing slurry suspension was continuously added thereto within the range of 0.5 to 6.0 ml. The interior of the autoclave was evacuated to discharge carbon dioxide. The mixture was subjected to centrifugal separation for 15 min. using a centrifugal separator at a rotation speed of 3,300 rpm. The obtained supernatant was further subjected to centrifugation at a rotation speed of 7,500 rpm for 50 min., whereby phospholipid membrane-magnetic vesicular particles having a grain size (R) shown in Table 2 were obtained as precipitates. The grain size (R) of the phospholipid membrane-magnetic vesicular particles was determined similarly to the foregoing manufacturing method of the lipid membrane-magnetic vesicular particles.

Manufacturing Method 5

Lipid having a maleimide group (EMC-DPPE) was prepared in accordance with Example 1 of JP-A No. 11-106391. Thus, 1.5 mg of the EMC-DPPE, 8.5 mg of phosphatidylethanolamine, 20 mg of phosphatidylcholine and 900 ml of ethanol were placed into a stainless steel autoclave and the interior of the autoclave was heated to 60° C., then, 13 g of liquid carbon dioxide was added thereto. The pressure in the interior of the autoclave was increased from 50 kg/cm$^2$ to 200 kg/cm$^2$ and lipid was allowed to be dissolved in the supercritical carbon dioxide, while stirring within the autoclave. Subsequently, physiological saline was added to the magnetic microparticles described in Table 2 to form a slurry suspension containing magnetic microparticles at a concentration of 10 µg/µl.

While stirring the supercritical carbon dioxide solution, the foregoing slurry suspension was continuously added thereto at 0.5-6.0 ml. The interior of the autoclave was evacuated to discharge the carbon dioxide.

To this solution, monoclonal antibody G-22 was attached in accordance with the method described in Example 1 of JP-A No. 11-106391. The mixture was subjected to centrifugal separation for 15 min. using a centrifugal separator at a rotation speed of 3,300 rpm. The obtained supernatant was further subjected to centrifugation at a rotation speed of 7,500 rpm for 50 min., whereby phospholipid membrane-magnetic vesicular particles having a grain size (R) shown in Table 2 were obtained as precipitates. The grain size (R) of the phospholipid membrane-magnetic vesicular particles was determined similarly to the foregoing manufacturing method of the lipid membrane-magnetic vesicular particles.

TABLE 2

| Magnetic Vesicular Particle No. | Manufacturing Method | Magnetic Microparticle | Particle Size r (nm) | Particle Size R (nm) | Size Ratio R/(r × 100) |
|---|---|---|---|---|---|
| Example 1 | 1 | 1 | 1 | 15 | 120 | 0.080 |
| Example 2 | 2 | 1 | 2 | 15 | 120 | 0.080 |
| Example 3 | 3 | 1 | 3 | 15 | 120 | 0.080 |
| Example 4 | 4 | 1 | 4 | 20 | 120 | 0.060 |
| Example 5 | 5 | 1 | 5 | 15 | 120 | 0.080 |
| Example 6 | 6 | 1 | 6 | 15 | 120 | 0.080 |
| Example 7 | 7 | 1 | 7 | 5 | 100 | 0.200 |
| Example 8 | 8 | 1 | 7 | 5 | 150 | 0.300 |
| Example 9 | 9 | 1 | 8 | 10 | 100 | 0.100 |
| Example 10 | 10 | 1 | 9 | 20 | 100 | 0.050 |
| Example 11 | 11 | 1 | 10 | 30 | 150 | 0.050 |
| Comparative Example 1 | 12 | 1 | 10 | 30 | 100 | 0.033 |
| Example 12 | 13 | 2 | 7 | 5 | 100 | 0.200 |
| Example 13 | 14 | 2 | 8 | 10 | 100 | 0.100 |
| Example 14 | 15 | 2 | 9 | 20 | 150 | 0.075 |
| Example 15 | 16 | 2 | 10 | 30 | 150 | 0.050 |
| Example 16 | 17 | 2 | 11 | 15 | 120 | 0.080 |
| Example 17 | 18 | 2 | 12 | 15 | 120 | 0.080 |
| Comparative Example 2 | 19 | 2 | 13 | 1 | 180 | 1.800 |
| Example 18 | 20 | 2 | 13 | 1 | 150 | 1.500 |
| Example 19 | 21 | 2 | 14 | 2.5 | 150 | 0.600 |
| Example 20 | 22 | 2 | 15 | 5 | 100 | 0.200 |
| Example 21 | 23 | 2 | 16 | 10 | 100 | 0.100 |
| Example 22 | 24 | 2 | 17 | 20 | 100 | 0.050 |
| Example 23 | 25 | 2 | 18 | 10 | 100 | 0.100 |
| Example 24 | 26 | 2 | 19 | 10 | 100 | 0.100 |
| Example 25 | 27 | 2 | 20 | 10 | 100 | 0.100 |
| Example 26 | 28 | 3 | 11 | 10 | 100 | 0.100 |
| Example 27 | 29 | 3 | 12 | 10 | 100 | 0.100 |
| Example 28 | 30 | 3 | 13 | 10 | 100 | 0.100 |
| Example 29 | 31 | 4 | 5 | 15 | 100 | 0.067 |
| Example 30 | 32 | 4 | 8 | 10 | 100 | 0.100 |
| Example 31 | 33 | 4 | 16 | 10 | 100 | 0.100 |
| Example 32 | 34 | 4 | 18 | 10 | 100 | 0.100 |
| Example 33 | 35 | 4 | 19 | 10 | 100 | 0.100 |
| Example 34 | 36 | 4 | 20 | 10 | 100 | 0.100 |
| Example 35 | 37 | 4 | 24 | 10 | 100 | 0.100 |
| Example 36 | 38 | 4 | 25 | 10 | 100 | 0.100 |
| Example 37 | 39 | 4 | 27 | 10 | 100 | 0.100 |
| Example 38 | 40 | 4 | 28 | 10 | 100 | 0.100 |
| Example 39 | 41 | 5 | 5 | 15 | 100 | 0.067 |
| Example 40 | 42 | 5 | 8 | 10 | 100 | 0.100 |
| Example 41 | 43 | 5 | 16 | 10 | 100 | 0.100 |
| Example 42 | 44 | 5 | 18 | 10 | 100 | 0.100 |
| Example 43 | 45 | 5 | 24 | 10 | 100 | 0.100 |
| Example 44 | 46 | 5 | 25 | 10 | 100 | 0.100 |
| Comparative Example 3 | 47 | 1 | 29 | 15 | 120 | 0.080 |
| Comparative Example 4 | 48 | 1 | 30 | 20 | 120 | 0.060 |
| Comparative Example 5 | 49 | 1 | 31 | 10 | 150 | 0.150 |
| Comparative Example 6 | 50 | 1 | 32 | 20 | 150 | 0.075 |
| Comparative Example 7 | 51 | 2 | 29 | 15 | 120 | 0.080 |
| Comparative Example 8 | 52 | 2 | 30 | 20 | 120 | 0.060 |
| Comparative Example 9 | 53 | 2 | 31 | 10 | 150 | 0.150 |
| Comparative Example 10 | 54 | 2 | 32 | 20 | 150 | 0.075 |

Using the lipid membrane-magnetic vesicular particles obtained above, the following tests (Tests 1-6) were conducted.

Test 1

The magnetic vesicular particles shown in Table 3 were each diluted with an isotonic glucose solution to a concentration of 10 mg iron/ml. This solution was injected into a vein of rabbits to which experimental tumor VX-2 was transplanted to their liver in different sizes. After the elapse of time shown in Table 3, the rabbits were observed in an ultrasonic imaging diagnostic apparatus to judge the size of discriminable liver cancer. Results thereof are shown in Table 3.

As can be seen from Table 3, it was proved that lipid membrane-magnetic vesicular particles of this invention had no problem with respect to discriminable tumor size, as compared to comparative examples and variation in size of discriminable tumor was less than in the comparative samples, even after an elapse of time.

TABLE 3

| Magnetic Vesicular Particle No. | Size of Discriminable Tumor (mm) | | | | |
|---|---|---|---|---|---|
| | After 30 min. | After 1 hr. | After 6 hr. | After 12 hr. | After 24 hr. |
| Example 1 | 1 | 5 | 5 | 8 | 10 | 10 |
| Example 2 | 2 | 5 | 5 | 8 | 10 | 10 |
| Example 3 | 3 | 5 | 5 | 8 | 10 | 10 |
| Example 4 | 4 | 5 | 5 | 8 | 10 | 10 |
| Example 5 | 5 | 5 | 5 | 8 | 10 | 10 |
| Example 6 | 6 | 5 | 5 | 8 | 10 | 10 |
| Example 7 | 7 | 5 | 5 | 8 | 10 | 10 |
| Example 8 | 8 | 5 | 5 | 8 | 10 | 10 |
| Example 9 | 9 | 5 | 5 | 8 | 10 | 10 |
| Example 10 | 10 | 5 | 5 | 8 | 10 | 10 |
| Example 12 | 13 | 5 | 5 | 5 | 8 | 10 |
| Example 13 | 14 | 5 | 5 | 5 | 8 | 10 |
| Example 14 | 15 | 5 | 5 | 5 | 8 | 10 |
| Example 15 | 16 | 5 | 5 | 5 | 8 | 10 |
| Example 16 | 17 | 5 | 5 | 5 | 8 | 10 |
| Example 17 | 18 | 5 | 5 | 5 | 8 | 10 |
| Comparative Example 2 | 19 | 8 | 10 | 10 | 15 | —*[1] |
| Example 18 | 20 | 5 | 5 | 5 | 8 | 10 |
| Example 19 | 21 | 5 | 5 | 5 | 8 | 10 |
| Example 20 | 22 | 5 | 5 | 5 | 8 | 10 |
| Example 21 | 23 | 5 | 5 | 5 | 8 | 10 |
| Example 22 | 24 | 5 | 5 | 5 | 8 | 10 |
| Example 23 | 25 | 5 | 5 | 5 | 8 | 10 |
| Example 24 | 26 | 5 | 5 | 5 | 8 | 10 |
| Example 25 | 27 | 5 | 5 | 5 | 8 | 10 |
| Comparative Example 3 | 47 | 5 | 10 | —*[1] | —*[1] | —*[1] |
| Comparative Example 4 | 48 | 5 | 8 | 10 | —*[1] | —*[1] |
| Comparative Example 5 | 49 | 5 | 8 | 10 | —*[1] | —*[1] |
| Comparative Example 6 | 50 | 5 | 8 | 10 | —*[1] | —*[1] |

*[1]Function as a contrast medium was not noted at all.

Test 2

The magnetic vesicular particles shown in Table 4 were each diluted with an isotonic glucose solution to a concentration of 10 mg iron/ml. This solution was locally injected into the breast cancer tumor site of mousses into which a cell line of human breast cancer was hypodermically transplanted. After the elapse of time as shown in Table 4, the rabbits were observed in a nuclear magnetic resonance imaging diagnostic apparatus to determine the size of discriminable tumors. Results thereof are shown in Table 4.

As can be seen from Table 4, it was proved that lipid membrane-magnetic vesicular particles of this invention were discriminable even after an elapse of time, as compared to comparative examples.

TABLE 4

| | Magnetic Vesicular Particle No. | Size of Discriminable Tumor (mm) | | | | |
|---|---|---|---|---|---|---|
| | | After 30 min. | After 1 hr. | After 6 hr. | After 12 hr. | After 24 hr. |
| Example 21 | 23 | 5 | 5 | 5 | 8 | 10 |
| Example 22 | 24 | 5 | 5 | 5 | 8 | 10 |
| Example 23 | 25 | 5 | 5 | 5 | 8 | 10 |
| Example 24 | 26 | 5 | 5 | 5 | 8 | 10 |
| Example 25 | 27 | 5 | 5 | 5 | 8 | 8 |
| Example 26 | 28 | 5 | 5 | 5 | 8 | 8 |
| Example 27 | 29 | 5 | 5 | 5 | 8 | 8 |
| Example 28 | 30 | 5 | 5 | 5 | 8 | 8 |
| Example 29 | 31 | 5 | 5 | 5 | 5 | 8 |
| Example 30 | 32 | 5 | 5 | 5 | 5 | 8 |
| Example 31 | 33 | 5 | 5 | 5 | 5 | 8 |
| Example 32 | 34 | 5 | 5 | 5 | 5 | 8 |
| Example 33 | 35 | 5 | 5 | 5 | 5 | 8 |
| Example 34 | 36 | 5 | 5 | 5 | 5 | 8 |
| Example 35 | 37 | 5 | 5 | 5 | 5 | 8 |
| Example 36 | 38 | 5 | 5 | 5 | 5 | 8 |
| Example 37 | 39 | 5 | 5 | 5 | 5 | 8 |
| Example 38 | 40 | 5 | 5 | 5 | 5 | 8 |
| Comparative Example 7 | 51 | 5 | 8 | 10 | 15 | —[*1] |
| Comparative Example 8 | 52 | 5 | 8 | 10 | 15 | —[*1] |
| Comparative Example 9 | 53 | 5 | 5 | 8 | 10 | 15 |
| Comparative Example 10 | 54 | 5 | 5 | 8 | 10 | 15 |

[*1] Function as a contrast medium was not noted at all.

Test 3

The magnetic vesicular particles shown in Table 5 were each diluted with an isotonic glucose solution to a concentration of 10 mg iron/ml. This solution was injected into a vein of rats into which a cell line of human malignant glioma had been transplanted. After an elapse of time as shown in Table 5, the rats were observed in a nuclear magnetic resonance imaging diagnostic apparatus to determine the size of discriminable tumors. Results thereof are shown in Table 5.

TABLE 5

| | Magnetic Vesicular Particle No. | Size of Discriminable Tumor (mm) | | | | | |
|---|---|---|---|---|---|---|---|
| | | After 30 min. | After 1 hr. | After 6 hr. | After 12 hr. | After 24 hr. | After 36 hr. |
| Example 13 | 14 | 5 | 5 | 5 | 8 | 10 | 10 |
| Example 23 | 25 | 5 | 5 | 5 | 8 | 10 | 10 |
| Example 29 | 31 | 5 | 5 | 5 | 5 | 8 | 10 |
| Example 30 | 32 | 5 | 5 | 5 | 5 | 8 | 10 |
| Example 31 | 33 | 5 | 5 | 5 | 5 | 8 | 10 |
| Example 32 | 34 | 5 | 5 | 5 | 5 | 8 | 10 |
| Example 35 | 37 | 5 | 5 | 5 | 5 | 8 | 10 |
| Example 36 | 38 | 5 | 5 | 5 | 5 | 8 | 10 |
| Example 39 | 41 | 5 | 5 | 5 | 5 | 5 | 8 |
| Example 40 | 42 | 5 | 5 | 5 | 5 | 5 | 8 |
| Example 41 | 43 | 5 | 5 | 5 | 5 | 5 | 5 |
| Example 42 | 44 | 5 | 5 | 5 | 5 | 5 | 8 |
| Example 43 | 45 | 5 | 5 | 5 | 5 | 5 | 5 |
| Example 44 | 46 | 5 | 5 | 5 | 5 | 5 | 5 |
| Comparative Example 7 | 51 | 5 | 5 | 8 | 10 | —[*1] | —[*1] |
| Comparative Example 8 | 52 | 5 | 5 | 8 | 10 | —[*1] | —[*1] |
| Comparative Example 9 | 53 | 5 | 5 | 8 | 8 | 10 | —[*1] |
| Comparative Example 10 | 54 | 5 | 5 | 8 | 8 | 10 | —[*1] |

[*1] Function as a contrast medium was not noted at all.

Test 4

The magnetic vesicular particles shown in Table 6 were each diluted with an isotonic glucose solution to a concentration of 10 mg iron/ml. This solution was locally injected into the breast cancer site of mousses into which a cell line of low molecular type line cancer, originated from human lung was transplanted immediately below the pleura. After 30 min. or 24 hr., exposure to an alternating magnetic field was conducted under the following conditions:

frequency: 375 Hz, coil to generate a magnetic field: 300 mm in diameter, magnetic field intensity: 6 mT, current: 225 A, output: 3 KW, and distance from an applicator: 20 mm.

A fiberoptic thermometer was arranged in and near the tumor site to determine temperatures of tumor and normal sites. The time of the tumor site reaching 43° C. was determined, at which time the temperature of the normal site was also determined. Results thereof are shown in Table 6.

As can be seen from Table 6, it was proved that when thermotherapy was conducted, the lipid membrane-magnetic vesicular particles of this invention efficiently raised the temperature of only the tumor site within a short period of time, enabling performance of efficient thermotherapy irrespective of elapse of time after local injection, as compared to comparative examples.

TABLE 6

| Magnetic Vesicular Particle No. | Normal Site Temperature[*1] (° C.) | Heating (1)[*2] | | Heating (2)[*3] | |
|---|---|---|---|---|---|
| | | Time[*4] (min) | Temperature[*5] (° C.) | Time[*4] (min) | Temperature[*5] (° C.) |
| Example 9 | 9 | 32.8 | 5.0 | 34.5 | 10.5 | 36.9 |
| Example 10 | 10 | 33.5 | 6.0 | 35.2 | 12.5 | 37.8 |
| Comparative Example 1 | 12 | 32.9 | 15.0 | 38.5 | 25.0 | 42.5 |
| Example 13 | 14 | 33.3 | 5.0 | 35.1 | 10.0 | 36.9 |
| Example 21 | 23 | 33.8 | 3.5 | 34.2 | 7.5 | 35.6 |
| Example 36 | 38 | 33.0 | 3.5 | 33.9 | 6.0 | 35.1 |
| Comparative Example 9 | 53 | 33.1 | 5.0 | 34.8 | 20.0 | 40.5 |

[*1] normal site temperature before subjected to alternating magnetic field heating
[*2] alternating magnetic field heating at 30 min after injection
[*3] alternating magnetic field heating at 24 hr. after injection
[*4] time necessary to reach 43° C.
[*5] normal site temperature (° C.)

Test 5

The magnetic vesicular particles shown in Table 7 were each diluted with an isotonic glucose solution to a concentration of 10 mg iron/ml. This solution was injected into veins of rats into which a cell line of human malignant glioma was transplanted. After 1 hr. or the time shown in Table 7, exposure to an alternating magnetic field was continuously conducted under the following conditions:

frequency: 370 Hz, applicator to generate a magnetic field: 310 mm in coil diameter, magnetic field intensity: 8 mT, current: 300 A, output: 5 KW, and distance from the applicator: 20 mm.

A fiberoptic thermometer was arranged in the tumor site to determine temperatures of the tumor and the normal site. The time of the tumor site reaching 43° C. was determined, at which time the temperature of the normal site was also determined. Results thereof are shown in Table 7.

conducted in a nuclear magnetic resonance imaging diagnostic apparatus to determine the size of a glioma tumor site from a diagnosis image. Results thereof are shown in Table 8. In any case of the foregoing, capability of achieving contrast as a contrast medium for tumor was at a level acceptable in practice.

TABLE 8

| | Magnetic Vesicular Particle | Size of Tumor (mm) | | |
|---|---|---|---|---|
| | No. | 1st (m) | 2nd (mm) | 3rd (mm) |
| Example 21 | 23 | 12 | 8 | —*1 |
| Example 23 | 25 | 11 | 8 | —*1 |
| Example 31 | 33 | 10 | 7 | —*1 |

TABLE 7

| | Magnetic Vesicular Particle No. | Normal Site Temperature*1 (° C.) | Heating (1)*2 | | Heating (2)*3 | | Heating (3)*4 | |
|---|---|---|---|---|---|---|---|---|
| | | | Time*5 (min) | Temperature*6 (° C.) | Time*5 (min) | Temperature*6 (° C.) | Time*5 (min) | Temperature*6 (° C.) |
| Example 13 | 14 | 33.5 | 5.0 | 34.8 | 12.0 | 37.6 | 25.0 | 42.4 |
| Example 23 | 25 | 32.6 | 5.0 | 34.4 | 10.0 | 36.8 | 18.0 | 39.8 |
| Example 29 | 31 | 33.1 | 5.0 | 34.3 | 8.5 | 36.8 | 15.0 | 38.4 |
| Example 30 | 32 | 33.0 | 5.0 | 35.0 | 8.5 | 36.4 | 15.0 | 38.9 |
| Example 31 | 33 | 32.6 | 4.0 | 34.5 | 7.0 | 35.4 | 13.0 | 37.5 |
| Example 35 | 37 | 32.8 | 4.0 | 34.3 | 7.0 | 35.9 | 12.0 | 37.4 |
| Example 36 | 38 | 33.5 | 3.5 | 34.1 | 5.5 | 35.1 | 13.0 | 37.9 |
| Example 39 | 41 | 33.4 | 3.5 | 34.4 | 5.0 | 34.9 | 10.0 | 36.5 |
| Example 40 | 42 | 33.1 | 3.5 | 33.8 | 5.0 | 34.7 | 10.0 | 36.3 |
| Example 41 | 43 | 32.9 | 3.0 | 33.5 | 4.0 | 34.6 | 7.0 | 35.5 |
| Example 43 | 45 | 33.0 | 3.0 | 33.9 | 3.5 | 34.1 | 5.0 | 34.8 |
| Example 44 | 46 | 33.4 | 3.0 | 33.7 | 3.5 | 34.3 | 5.0 | 34.6 |
| Comparative Example 9 | 53 | 33.2 | 5.0 | 34.8 | —*7 | —*7 | —*7 | —*7 |

*1 normal site temperature before subjected to alternating magnetic field heating
*2 alternating magnetic field heating at 1 hr. after injection
*3 alternating magnetic field heating at 6 hr. after injection
*4 alternating magnetic field heating at 24 hr. after injection
*5 time necessary to reach 43° C.
*6 normal site temperature (° C.)
*7 no temperature increase even after subjected to alternating magnetic field heating for 30 min.

As can be seen from Table 7, it was proved that when thermotherapy was conducted, the lipid membrane-magnetic vesicular particles of this invention efficiently raised a temperature of only a tumor site within a short period of time, as compared to the comparative examples. It was further shown that enhanced accumulation at the tumor site enables performance of efficient therapy without newly supplying magnetic grains when applying therapy a few times.

Test 6

The magnetic vesicular particles shown in Table 8 were each diluted with an isotonic glucose solution to a concentration of 10 mg iron/ml. This solution was injected through intravenous injection to mousses into which a cell line of human breast cancer was hypodermically transplanted. After 2 hr. and 24 hr., exposure to an alternating magnetic field was conducted similarly to the foregoing test 5. After 6 days since the first intravenous injection, a second intravenous injection was conducted, and again after 2 hr. and 24 hr., exposure to an alternating magnetic field was conducted similarly to the foregoing test 5. Again, after 15 days since the second intravenous injection, a third intravenous injection was conducted.

After 1 hr. since the respective first, second and third injections of the magnetic vesicular particles, observation was TABLE 8-continued

| | Magnetic Vesicular Particle | Size of Tumor (mm) | | |
|---|---|---|---|---|
| | No. | 1st (m) | 2nd (mm) | 3rd (mm) |
| Example 32 | 34 | 12 | 7 | —*1 |
| Example 35 | 37 | 11 | 7 | —*1 |
| Example 36 | 38 | 11 | 7 | —*1 |
| Example 41 | 43 | 10 | 5 | —*1 |
| Example 42 | 44 | 12 | 6 | —*1 |
| Example 43 | 45 | 10 | 5 | —*1 |
| Example 44 | 46 | 12 | 5 | —*1 |
| Comparative Example 9 | 53 | 11 | 9 | 6 |

*1 no tumor was noted in nuclear magnetic resonance imaging diagnosis

As can be seen from Table 8, it was proved that magnetic vesicular particles of this invention can not only provide both functions as an imaging agent (or contrast medium) and a therapeutic agent but also efficiently function as a therapeutic agent.

The invention claimed is:

1. A method of manufacturing a preparation containing magnetic vesicular particles, the method comprising:
   (a) mixing at least one lipid membrane constituent and a supercritical carbon dioxide to form a mixture,
   (b) adding to the mixture a dispersion containing magnetic nanoparticles to which an organic compound is bonded, and
   (c) discharging the carbon dioxide to form the magnetic vesicular particles including the magnetic nanoparticles within a lipid membrane, wherein the magnetic vesicular particles, each includes at least one magnetic nanoparticle within a lipid membrane, an organic compound having at least two groups selected from the group consisting of a hydroxyl group, a carboxyl group, a carbamoyl group, an amino group, a mercapto group, a sulfo group, a dithio group, a thiocarboxyl group and a dithiocarboxyl group is bonded to the magnetic nanoparticle, and the magnetic vesicular particles satisfy the following equation:

$$0.05 \leq R/(r \times 100) \leq 1.5$$

wherein R represents an average grain size of the magnetic vesicular particles and r represents an average particle size of magnetic nanoparticles included in the magnetic vesicular particles wherein the organic compound is a compound selected from the group consisting of phthalic acid, isophthalic acid, therephthalic acid, succinic acid, glutaric acid, adipic acid, pimelic acid, fumaric acid, maleic acid, 2-mercaptoamine, 6-aminehexanethiol, 2-mercaptopropionic acid, asparagic acid, glutamine, malic acid, oxaloacetic acid, 2-ketoglutaric acid, serine, threonine, cysteine, cysteic acid, cystine, N-acetylcysteine, cysteine ethyl ester, and dithiothreitol.

2. The method of claim 1, wherein the magnetic vesicular particles satisfy the following equation:

$$0.05 \leq R/(r \times 100) \leq 1.0$$

wherein R and r are the same as defined in claim 1.

3. The method of claim 1, wherein the magnetic nanoparticles have an average particle size of 1 to 30 nm and are comprised of a ferrite.

4. The method of claim 1, wherein the magnetic vesicular particles are liposomes formed of the lipid membrane and including at least one magnetic nanoparticle within the lipid membrane.

5. The method of claim 4, wherein the liposomes exhibit a positive surface charge.

6. The method of claim 1, wherein the preparation further comprises an imaging agent or a therapeutic agent for a tumor.

7. The method of claim 6, wherein the therapeutic agent for a tumor is bonded directly or through a linking material to the lipid membrane.

8. The method of claim 6, wherein the imaging agent is a contrast medium for use in ultrasonic imaging diagnosis, nuclear magnetic resonance imaging diagnosis or X-ray imaging diagnosis.

* * * * *